United States Patent
Fraser et al.

(10) Patent No.: US 7,125,848 B2
(45) Date of Patent: Oct. 24, 2006

(54) METHODS OF TREATING NON-INFLAMMATORY GASTROINTESTINAL TRACT DISORDERS USING CAV2.2 SUBUNIT CALCIUM CHANNEL MODULATORS

(75) Inventors: Matthew Oliver Fraser, Apex, NC (US); Steven B. Landau, Wellesley, MA (US); Edward C. Burgard, Chapel Hill, NC (US)

(73) Assignee: Dynogen Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 10/865,225

(22) Filed: Jun. 10, 2004

(65) Prior Publication Data

US 2005/0026835 A1    Feb. 3, 2005

Related U.S. Application Data

(60) Provisional application No. 60/478,671, filed on Jun. 13, 2003.

(51) Int. Cl.
*A01N 37/18*   (2006.01)
*A61K 38/00*   (2006.01)
*C07K 14/00*   (2006.01)

(52) U.S. Cl. .............. 514/12; 514/2; 530/350
(58) Field of Classification Search ........... 530/350; 514/12
See application file for complete search history.

(56) References Cited

U.S. PATENT DOCUMENTS

| | | | |
|---|---|---|---|
| 5,670,622 A | 9/1997 | Shon et al. | |
| 5,739,276 A | 4/1998 | Shon et al. | |
| 6,077,680 A | 6/2000 | Kem et al. | |
| 6,190,691 B1 | 2/2001 | Mak | |
| 2002/0002167 A1* | 1/2002 | Niwa et al. | 514/252.03 |

FOREIGN PATENT DOCUMENTS

| | | |
|---|---|---|
| EP | 0 997 147 A1 | 5/2000 |
| EP | 1 042 468 A2 | 10/2000 |
| EP | 1 117 680 A2 | 7/2001 |
| EP | 1 191 022 A1 | 3/2002 |
| EP | 1 318 147 A1 | 6/2003 |
| GB | 2 262 886 A | 7/1993 |
| WO | WO 95/23132 | 8/1995 |
| WO | WO 96/33206 | 10/1996 |
| WO | WO 98/23639 | 6/1998 |
| WO | WO 98/54123 | 12/1998 |
| WO | WO 99/28342 | 6/1999 |
| WO | WO 00/06559 | 2/2000 |
| WO | WO 00/18801 | 4/2000 |
| WO | WO 02/36567 A1 | 5/2002 |
| WO | WO 03/018561 A1 | 3/2003 |
| WO | WO 2004/080444 A2 | 9/2004 |

OTHER PUBLICATIONS

Borderies et al., Effect of Different Calcium Channel Blockers on Inhibitory Junction Potentials and Slow Waves Porcine Ileum, Life Sciences (1997), 60(2), p. 883-892.*
Catterall, W.A., "Structure and Regulation of Voltage-Gated $Ca^{2+}$ Channels," *Annu. Rev. Cell Dev. Biol.*, 2000, pp. 521-555, vol. 16.

* cited by examiner

*Primary Examiner*—Robert A. Wax
*Assistant Examiner*—Rita Mitra
(74) *Attorney, Agent, or Firm*—Alston & Bird LLP

(57) ABSTRACT

A method is provided for using Cav2.2 subunit calcium channel modulators to treat non-inflammatory gastrointestinal tract disorders.

14 Claims, 1 Drawing Sheet

METHODS OF TREATING NON-INFLAMMATORY GASTROINTESTINAL TRACT DISORDERS USING CAV2.2 SUBUNIT CALCIUM CHANNEL MODULATORS

CROSS-REFERENCE TO RELATED APPLICATIONS

This application claims the benefit of U.S. Provisional Application No. 60/478,671, filed Jun. 13, 2003; which is hereby incorporated by reference.

FIELD OF THE INVENTION

The invention relates to methods of using Cav2.2 subunit calcium channel modulators to treat non-inflammatory gastrointestinal tract disorders, particularly non-inflammatory structural GI tract disorders and non-structural GI tract disorders.

BACKGROUND OF THE INVENTION

Gastrointestinal (GI) tract disorders affect the quality of life of millions of men and women in the United States every year. GI tract disorders may involve disturbances of the GI smooth muscle, epithelium, sensory afferent neurons, or central nervous system pathways. In spite of the uncertainty regarding whether central or peripheral mechanisms, or both, are involved in GI tract disorders, many proposed mechanisms implicate neurons and pathways that mediate visceral sensation. Viscerosensory information from the GI tract is relayed by sensory fibers that enter the spinal cord via the dorsal root ganglion (DRG) or project to the nodose ganglion via vagal afferents (Physiology, ed. R. M Berne and M. N. Levy, 1983, CV Mosby Co. St. Louis). A number of different subtypes of sensory afferent neurons may be involved in neurotransmission from the GI tract. These may be classified as, but not limited to, small diameter, medium diameter, large diameter, myelinated, unmyelinated, sacral, lumbar, DRG, vagal, nodose, peptidergic, non-peptidergic, IB4 positive, IB4 negative, C fiber, A$\delta$ fiber, A$\beta$ fiber, high threshold or low threshold neurons.

GI tract disorders have been characterized as structural (or mucosal) GI tract disorders and non-structural (or non-mucosal) GI tract disorders. Structural disorders include inflammatory bowel disorders and non-inflammatory structural GI tract disorders. Non-structural disorders include a variety of disorders classified as functional GI tract disorders.

Inflammatory bowel disorders include a group of disorders that can cause inflammation or ulceration of the GI tract. Ulcerative colitis and Crohn's disease are the most common types of inflammatory bowel disorders, although collagenous colitis, lymphocytic (microscopic) colitis, and other disorders have also been described.

Ulcerative colitis is a chronic inflammatory disorder of unknown etiology afflicting the large intestine and, except when very severe, is limited to the bowel mucosa. The course of this disorder may be continuous or relapsing and may be mild or severe. Medical treatment primarily includes the use of salicylate derivatives, glucocorticosteroids such as prednisone or prednisone acetate and anti-metabolites dependent on the clinical state of the patient. Salicylate derivatives, such as sulphazine or mesalamine, are efficacious in patients with mild cases of the disorder. Glucocorticosteroids and anti-metabolites are efficacious in patients with moderate or severe disease but are associated with a number of side effects. Patients who need chronic doses of glucocorticosteroids or anti-metabolites for control of their disorder eventually undergo removal of the colon surgically to eliminate the disease.

Like ulcerative colitis, Crohn's disease (also known as regional enteritis, ileitis, or granulomatous ileocolitis) is a chronic inflammatory disorder of unknown etiology; however the location and pathology of the disease differ. Crohn's disease typically presents in either the small intestine, large intestine or the combination of the two locations and can cause inflammation deeper into the muscle and serosa located within the intestinal wall. The course of the disorder may be continuous or relapsing and may be mild or severe. Medical treatment includes the continuous use of salicylate derivatives, glucocorticosteroids, anti-metabolites, and administration of an anti-TNF antibody. Many Crohn's disease patients require intestinal surgery for a problem related to the disease, but unlike ulcerative colitis subsequent relapse is common.

Collagenous colitis and lymphocytic colitis are idiopathic inflammatory disorders of the colon that cause watery diarrhea typically in middle-aged or older individuals. Lymphocytic colitis is distinguished from collagenous colitis by the absence of a thickened subepithelial collagenous layer. Bismuth in the form of Pepto-Bismol may be an effective treatment in some patients, although more severe cases may require the use of salicylate derivatives, antibiotics such as metronidazole, and glucocorticosteroids.

Functional GI tract disorders are characterized by presentation of abdominal-type symptoms without evidence of changes in metabolism or structural abnormalities. Disorders that are typically considered under functional disorders include dysphagia, non-ulcer dyspepsia, irritable bowel syndrome, slow-transit constipation, and evacuation disorders (Camilleri (2002) Gastrointestinal Motility Disorders, In *WebMD Scientific American Medicine*, edited by David C. Dale and Daniel D. Federman, New York, N.Y., WebMD). A prominent example of a functional GI tract disorder is irritable bowel syndrome (IBS), also known by a variety of synonyms, including functional bowel, pylorospasm, nervous indigestion, spastic colon, spastic colitis, spastic bowel, intestinal neurosis, functional colitis, irritable colon, mucous colitis, laxative colitis, and functional dyspepsia. IBS generally leads to abdominal pain and/or discomfort and an alteration in bowel habit with no clear etiology. Diagnosis relies on Rome criteria taking into account all symptoms related to patient presentation. (See, e.g., Drossman et al. (1997) *Gastroenterology*, 112: 2120). Patients typically present with symptoms consistent with hyperalgesia and allodynia.

At present, treatments for IBS have been largely ineffective, and have included stress management, diet, and drugs. Psychoactive drugs, such as anxiolytics and antidepressants, have been utilized but have limited utility because of the side effect profile. Antispasmodics and various antidiarrheal preparations have also been used but these remain as unsatisfactory remedies to patients with IBS.

Non-ulcer dyspepsia (NUD) is another prominent example of a functional GI tract disorder with no established etiology. Symptoms related to NUD include nausea, vomiting, pain, early satiety, bloating and loss of appetite. Altered gastric emptying and increased gastric sensitivity and distress may contribute to NUD but do not completely explain its presentation. Treatments include behavioral therapy, psychotherapy, or administration of antidepressants, motility regulatory agents, antacids, H$_2$-receptor antagonists, and, prokinetics. However, many of these treatments have shown limited efficacy in many patients.

In addition to the structural/non-structural classification described above, GI tract disorders may also be sub-classified based upon anatomical, physiological, and other characteristics of different portions of the GI tract as described in Sleisenger and Fordtran's Gastrointestinal and Liver Disease, 6th Ed. (W.B. Saunders Co. 1998); K. M. Sanders (1996) *Gastroenterology*, 111: 492–515; P. Holzer (1998) *Gastroenterology*, 114: 823–839; and R. K. Montgomery et al. (1999) *Gastroenterology*, 116: 702–731. For example, acid peptic disorders are generally thought to arise from damage due to acidic and/or peptic activity of gastric secretions and may affect the esophagus, stomach, and duodenum. Acid peptic disorders include gastroesophageal reflux disease, peptic ulcers (both gastric and duodenal), erosive esophagitis and esophageal stricture. Zollinger-Ellison Syndrome may be considered an acid peptic disorder since it typically presents with multiple ulcers due to excessive acid secretion caused by a endocrine tumor. Treatments typically include gastric acid suppressive therapies, antibiotics, and surgery. In some patients, however, these therapies have proven ineffective.

Another sub-classification for GI tract disorders may be drawn between gastroesophageal and intestinal disorders based upon characteristics between different portions of the GI tract as disclosed in Sleisenger and Fordtran's Gastrointestinal and Liver Disease, $_6^{th}$ Ed. (W.B. Saunders Co. 1998); K. M. Sanders (1996) *Gastroenterology*, 111: 492–515; P. Holzer (1998) *Gastroenterology*, 114: 823–839; and R. K. Montgomery et al. (1999) *Gastroenterology*, 116: 702–731. Structural gastroesophageal disorders include disorders of the stomach and/or esophagus where there is no evidence of structural perturbations (including those observed in the mucosa) distal to the pylorus. Dyspepsia (chronic pain or discomfort centered in the upper abdomen) is a prominent feature of most structural gastroesophageal disorders but can also be observed in non-structural perturbations, and has been estimated to account for 2 to 5 percent of all general practice consultations. Structural gastroesophageal disorders include gastritis and gastric cancer. By contrast, Structural intestinal tract disorders occur in both the small intestine (the duodenum, jejunum, and ileum) and in the large intestine. Structural intestinal tract disorders are characterized by structural changes in the mucosa or in the muscle layers of the intestine, and include non-peptic ulcers of the small intestine, malignancies, and diverticulosis. Non-peptic ulcers in the small intestine are typically related to administration of non-steroidal anti-inflammatory drugs. Diverticulosis is a disorder that rarely occurs in the small intestine and most commonly appears in the colon.

Because existing therapies and treatments for GI tract disorders are associated with limitations as described above, new therapies and treatments are therefore desirable.

SUMMARY OF THE INVENTION

The present invention relates to methods and compositions for the treatment of non-inflammatory GI tract disorders, particularly non-inflammatory structural GI tract disorders and non-structural GI tract disorders. Specifically, treatment of non-inflammatory GI tract disorders using Cav2.2 subunit calcium channel modulators is described.

Non-inflammatory structural GI tract disorders that may be treated according to the present invention include, but are not limited to, hiatal hernias, strictures, esophageal webs, Schatzki's ring, esophageal diverticula, and esophageal scleroderma. Non-structural GI tract disorders that may be treated according to the present invention include, but are not limited to, motor disorders of the esophagus such as achalasia and diffuse esophageal spasm, and functional GI tract disorders such as irritable bowel syndrome.

Compositions of the invention comprise Cav2.2 subunit calcium channel modulators and other peptide, non-peptide, and peptidomimetic drug-like molecules that bind to Cav2.2-containing calcium channels, as well as pharmaceutically acceptable, pharmacologically active salts, esters, amides, prodrugs, active metabolites, enantiomers, diastereomers, and other derivatives thereof.

The compositions are administered in therapeutically effective amounts to a patient in need thereof for treating non-inflammatory GI tract disorders. It is recognized that the compositions may be administered by any means of administration as long as an effective amount for the treatment of non-inflammatory GI tract disorders is delivered. The compositions may be formulated, for example, for sustained, continuous, or as-needed administration.

BRIEF DESCRIPTION OF THE DRAWINGS

FIG. 1.

DETAILED DESCRIPTION OF THE INVENTION

Overview and Definitions

Figure 1A:
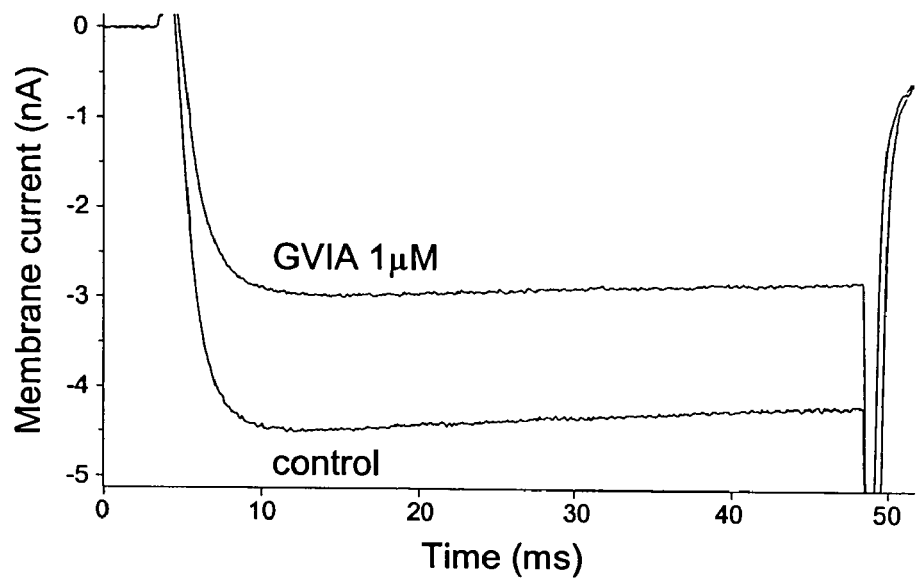
FIG. 1A depicts HVA calcium currents in dorsal root ganglion neurons innervating the colon induced by depolarizing pulses (−80 to 0 mV) before (control) and after application of Omega-conotoxin GVIA.
Figure 1B:
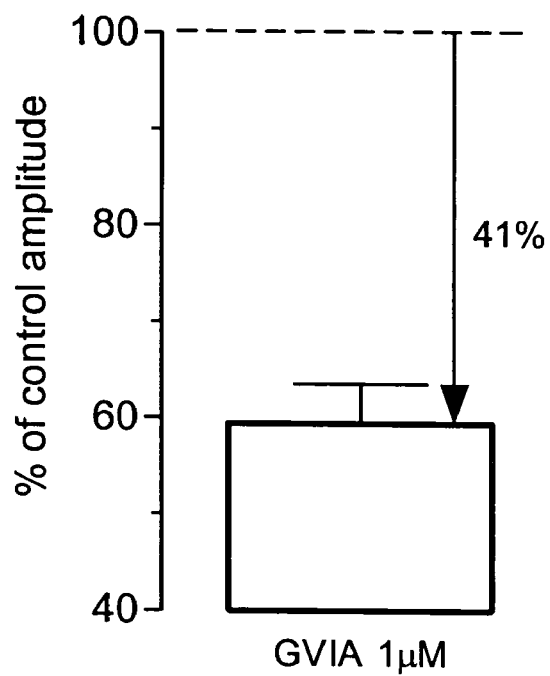
FIG. 1B depicts changes in peak calcium current following application of Omega-conotoxin GVIA expressed as percentage of control peak calcium current amplitude.

The present invention provides compositions and methods for treating non-inflammatory GI tract disorders, particularly non-inflammatory structural GI tract disorders and non-structural GI tract disorders. The compositions comprise a therapeutically effective dose of a Cav2.2 subunit calcium channel modulator. The methods are accomplished by administering, for example, various compositions and formulations that contain quantities of a Cav2.2 subunit calcium channel modulator and other peptide, non-peptide, and peptidomimetic drug-like molecules that interact with Cav2.2-containing calcium channels.

Before describing the present invention in detail, it is to be understood that this invention is not limited to specific active agents, dosage forms, dosing regimens, or the like, as such may vary. It is also to be understood that the terminology used herein is for the purpose of describing particular embodiments only, and is not intended to be limiting.

It must be noted that as used in this specification and the appended embodiments, the singular forms "a," "an" and "the" include plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

The term "structural GI tract disorder" or "mucosal GI tract disorder" refers to any GI tract disorder related to structural or mucosal abnormalities of the GI tract or where there is evidence of a related metabolic disturbance, including but not limited to inflammatory bowel disorders, structural gastroesophageal disorders, and structural intestinal disorders.

By "inflammatory GI disorder" is intended any disorder primarily associated with inflammation of the GI tract, including but not limited to inflammatory bowel disorder.

By "inflammatory bowel disorder" is intended any disorder primarily associated with inflammation of the small and/or large intestine, including but not limited to ulcerative colitis, Crohn's disease, ileitis, proctitis, celiac disease (or non-tropical sprue), enteropathy associated with seronegative arthropathies, microscopic or collagenous colitis, eosinophilic gastroenteritis, or pouchitis resulting after proctocolectomy, and post ileoanal anastomosis.

"Crohn's disease" is used in its conventional sense to refer to gastrointestinal inflammation primarily of the small and large intestine, including disorders with fistulas or with extraintestinal manifestations, and encompasses all synonyms including regional enteritis, ileitis, and granulomatous ileocolitis.

"Proctitis" is used in its conventional sense to refer to inflammation of the rectal lining.

"Celiac disease" is used in its conventional sense to refer to any disorder primarily associated with altered sensititivity to gluten or gluten byproducts, with or without alterations in small bowel morphology (typically villus blunting) and encompasses all synonyms including celiac sprue and non-tropical sprue. Patients diagnosed with celiac disease may have symptomatic gluten intolerance with prominent diarrhea and abdominal pain or with minimal symptoms such as abdominal discomfort and associated dermatitis herpetiformis.

"Colitis" is used in its conventional sense to refer to inflammation of the large intestine.

"Ulcerative colitis" is used in its conventional sense to refer to inflammation and ulcers in the top layers of the lining of the large intestine and can be of any extent, including proctitis, proctosigmoiditis, left-sided colitis, or pan-colitis.

"Collagenous colitis" or "microscopic colitis" is used in its conventional sense to refer to an inflammatory disorder of unknown etiology with watery diarrhea as the leading symptom. A biopsy of the intestine typically demonstrates a thicker-than-normal layer of collagen (connective tissue) just beneath the inner surface of the colon (the epithelium) and/or inflammation of the epithelium and of the layer of connective tissue that lies beneath the epithelium. There is an association of arthritis with this disorder.

"Eosinophilic gastroenteritis" is used in its conventional sense to refer to a condition where a biopsy of the GI tract demonstrates infiltration with a type of white blood cell called eosinophils. There is no single cause of eosinophilic gastroenteritis and in many cases there is no known cause. Symptoms may include feeling full before finishing a meal, diarrhea, abdominal cramping or pain, nausea and vomiting. Asthma and allergies are sometimes related to the disorder.

"Pouchitis" is used in its conventional sense to refer to inflammation in a distal location of the intestine after a surgery on the intestine.

"Collagenous colitis" is used in its conventional sense to refer to inflammation of the large intestine accompanied by a thickened subepithelial collagenous layer of the large intestine.

"Lymphocytic colitis" is used in its conventional sense to refer to inflammation of the large intestine without ulceration, and encompasses all synonyms including microscopic colitis.

By "non-inflammatory GI disorder" is intended any disorder of the GI tract not primarily associated with inflammation of the GI tract, including but not limited to non-inflammatory structural GI tract disorders and non-structural GI tract disorders. .

The term "non-inflammatory structural GI disorder" refers to any structural GI tract disorder as disclosed elsewhere herein that is not primarily associated with inflammation of the GI tract, including but not limited to hiatal hernias, strictures, esophageal webs, Schatzki's ring, esophageal diverticula, and esophageal scleroderma.

The term "non-structural GI tract disorder" or "non-mucosal GI tract disorder" refers to any GI tract disorder not related to structural or mucosal abnormalities of the GI tract, nor where there is evidence of a related metabolic disturbance, including but not limited to motor disorders of the esophagus such as achalasia and diffuse esophageal spasm, and functional GI tract disorders.

By "functional GI tract disorder" is intended any GI tract disorder associated with a disturbance of motor or sensory function in the absence of mucosal or structural damage or in the absence of a metabolic disorder. Functional GI tract disorders include functional dysphagia, non-ulcer dyspepsia, irritable bowel syndrome (IBS), slow-transit constipation and evacuation disorders.

By "non-ulcer dyspepsia" is intended any disorder associated with any abdominal symptom after eating including nausea, vomiting, pain, early satiety, bloating and loss of appetite where no ulceration in present in the esophagus, stomach or duodenum. Altered gastric emptying, increased gastric sensitivity and distress are considered as factors in the development of non-ulcer dyspepsia.

By "irritable bowel syndrome" or "IBS" is intended any disorder associated with abdominal pain and/or abdominal discomfort and an alteration in bowel habit, and encompasses all synonyms including functional bowel, pylorospasm, nervous indigestion, spastic colon, spastic colitis, spastic bowel, intestinal neurosis, functional colitis, irritable colon, mucous colitis, laxative colitis, and functional dyspepsia.

By "slow-transit constipation" is intended as a disorder with slowing of motility in the large intestine with a prolonged transit time through the organ.

By "evacuation disorders" is intended as any disorder where defecation occurs poorly and the patient is unable to expel stool.

By "acid peptic disorder" is intended any disorder associated with damage due to acidic and/or peptic activity of gastric secretions that affect the esophagus, stomach, and/or duodenum. Acid peptic disorders include gastroesophageal reflux disease, peptic ulcers (both gastric and duodenal), erosive esophagitis, esophageal strictures, and Zollinger-Ellison Syndrome.

GI tract disorders may divided between gastroesophageal and intestinal disorders based upon anatomical, physiological, and other characteristics of different portions of the GI tract as disclosed in Sleisenger and Fordtran's Gastrointestinal and Liver Disease, 6$^{th}$ Ed. (W.B. Saunders Co. 1998); K. M. Sanders (1996) *Gastroenterology*, 111: 492–515; P. Holzer (1998) *Gastroenterology*, 114: 823–839; and R. K. Montgomery et al. (1999) *Gastroenterology*, 116: 702–731.

By "gastroesophageal" is intended all parts of the esophagus and stomach. By "gastroesophageal disorders" is intended any disorder involving the esophagus and/or duodenum. By "structural gastroesophageal disorder" is intended any disorder of the stomach and/or esophagus where there is no evidence of structural perturbations (including those observed in the mucosa) distal to the pylorus. Structural gastroesophageal disorders include gastric cancer and gastritis.

By "intestinal tract" is intended all parts of the duodenum, jejeunum, ileum and large intestine (or colon). By "intestinal tract disorder" is intended any disorder involving the duodenum, jejeunum, ileum, and large intestine (or colon). By "structural intestinal tract disorder" is intended any disorder involving the duodenum, jejeunum, ileum, and/or large intestine (or colon) where important mucosal and structural abnormalities are present or there is evidence of a related metabolic disturbance that is not an inflammatory bowel disorder or an acid peptic disorder. Structural intestinal disorders include ulcers typically related to medications such as non-steroidal anti-inflammatory drugs, malignancies, and diverticulosis.

By "small intestine" is intended all parts of the duodenum, jejunum, and ileum.

The term "duodenum" is used in its conventional sense to refer to that portion of the GI tract beginning at the pylorus and ending at the ligament of Treitz. The duodenum is divided into four parts. (See, e.g., Yamada (1999) Textbook of Gastroenterology 3d Ed., Lippincott Williams & Wilkins). The first part of the duodenum is also known as the superior portion of the duodenum, and begins at the pylorus, is about 5 cm long, and passes backward and upward beneath the liver to the neck of the gallbladder (the first 2–3 cm of which is the duodenal bulb). The second part of the duodenum is also known as the descending portion of the duodenum, and extends along the right margin of the head of the pancreas, and is approximately 7 to 10 cm in length. The third part of the duodenum is also known as the horizontal portion of the duodenum, and is where the duodenum passes from right to left across the spine, inclining upwards for about 5 to 8 cm. The fourth part of the duodenum is also known as the ascending portion of the duodenum and begins at the left of the vertebral column, ascends to the left of the aorta for 2 to 3 cm and ends at the ligament of Treitz.

The terms "active agent" and "pharmacologically active agent" are used interchangeably herein to refer to a chemical compound that induces a desired effect, i.e., in this case, treatment of non-inflammatory GI tract disorders. The primary active agents herein are compounds that modulate Cav2.2 calcium channel subunits. In addition, a combination therapy wherein a compound that modulates Cav2.2 calcium channel subunits is administered with one or more additional active agents is also within the scope of the present invention. Such combination therapy may be carried out by administration of the different active agents in a single composition, by concurrent administration of the different active agents in different compositions, or by sequential administration of the different active agents. Included are derivatives and analogs of those compounds or classes of compounds specifically mentioned that also induce the desired effect.

The term "Cav2.2 subunit calcium channel modulator" as used herein is intended an agent that is capable of interacting with the Cav2.2 subunit of a calcium channel, including a binding event, to produce a physiological effect, such as opening, closing, blocking, up-regulating expression, or down-regulating expression of the channel. Unless otherwise indicated, the term "Cav2.2 subunit calcium channel modulator" is intended to include ω-conotoxin GVIA, ω-conotoxin ω-conotoxin CNVIIA, ω-conotoxin CVIID, ω-conotoxin AM336, cilnidipine, amlodipine, L-cysteine derivative 2A, ω-agatoxin IVA, N,N-dialkyl-dipeptidylamines, SNX-111, and Ziconotide, and other peptide, non-peptide, and peptidomimetic drug-like molecules that interact with Cav2.2-containing calcium channels as disclosed further herein, as well as salts, esters, amides, prodrugs, active metabolites, enantiomers, diastereomers, and other derivatives thereof. Further, it is understood that any salts, esters, amides, prodrugs, active metabolites or other derivatives are pharmaceutically acceptable as well as pharmacologically active.

The term "peptidomimetic" is used in its conventional sense to refer to a molecule that mimics the biological activity of a peptide but is no longer peptidic in chemical nature, including molecules that lack amide bonds between amino acids, as well as pseudo-peptides, semi-peptides and peptoids. Peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems that are similar to the biological activity of the peptide.

The term "anticholinergic agent" as used herein refers to any acetylcholine receptor antagonist, including antagonists of nicotinic and/or muscarinic acetylcholine receptors. The term "antinicotinic agent" as used herein is intended any nicotinic acytylcholine receptor antagonist. The term "antimuscarinic agent" as used herein is intended any muscarinic acetylcholine receptor antagonist. Unless otherwise indicated, the terms "anticholinergic agent," "antinicotinic agent," and "antimuscarinic agent" are intended to include anticholinergic, antinicotinic, and antimuscarinic agents as disclosed further herein, as well as salts, esters, amides, prodrugs, active metabolites, enantiomers, diastereomers, and other derivatives thereof. Further, it is understood that any salts, esters, amides, prodrugs, active metabolites or other derivatives are pharmaceutically acceptable as well as pharmacologically active.

The term "β3 adrenergic agonist" is used in its conventional sense to refer to a compound that binds to and agonizes β3 adrenergic receptors. Unless otherwise indicated, the term "β3 adrenergic agonist" is intended to include β3 adrenergic agonist agents as disclosed further herein, as well as salts, esters, amides, prodrugs, active metabolites, enantiomers, diastereomers, and other derivatives thereof. Further, it is understood that any salts, esters, amides, prodrugs, active metabolites or other derivatives are pharmaceutically acceptable as well as pharmacologically active.

The term "spasmolytic" (also known as "antispasmodic") is used in its conventional sense to refer to a compound that relieves or prevents muscle spasms, especially of smooth muscle. Unless otherwise indicated, the term "spasmolytic" is intended to include spasmolytic agents as disclosed further herein, as well as salts, esters, amides, prodrugs, active metabolites, enantiomers, diastereomers, and other derivatives thereof. Further, it is understood that any salts, esters, amides, prodrugs, active metabolites or other derivatives are pharmaceutically acceptable as well as pharmacologically active.

The term "neurokinin receptor antagonist" is used in its conventional sense to refer to a compound that binds to and antagonizes neurokinin receptors. Unless otherwise indicated, the term "neurokinin receptor antagonist" is intended to include neurokinin receptor antagonist agents as disclosed further herein, as well as salts, esters, amides, prodrugs, active metabolites, enantiomers, diastereomers, and other derivatives thereof. Further, it is understood that any salts, esters, amides, prodrugs, active metabolites or other derivatives are pharmaceutically acceptable as well as pharmacologically active.

The term "bradykinin receptor antagonist" is used in its conventional sense to refer to a compound that binds to and antagonizes bradykinin receptors. Unless otherwise indicated, the term "bradykinin receptor antagonist" is intended to include bradykinin receptor antagonist agents as disclosed further herein, as well as salts, esters, amides, prodrugs, active metabolites, enantiomers, diastereomers, and other derivatives thereof. Further, it is understood that any salts, esters, amides, prodrugs, active metabolites or other derivatives are pharmaceutically acceptable as well as pharmacologically active.

The term "nitric oxide donor" is used in its conventional sense to refer to a compound that releases free nitric oxide when administered to a patient. Unless otherwise indicated, the term "nitric oxide donor" is intended to include nitric oxide donor agents as disclosed further herein, as well as salts, esters, amides, prodrugs, active metabolites, enantiomers, diastereomers, and other derivatives thereof. Further, it is understood that any salts, esters, amides, prodrugs, active metabolites or other derivatives are pharmaceutically acceptable as well as pharmacologically active.

The terms "treating" and "treatment" as used herein refer to relieving the symptoms or lessening the discomfort associated with non-inflammatory GI tract disorders.

By an "effective" amount or a "therapeutically effective amount" of a drug or pharmacologically active agent is meant a nontoxic but sufficient amount of the drug or agent to provide the desired effect, i.e., relieving the symptoms or lessening the discomfort associated with non-inflammatory GI tract disorders. It is recognized that the effective amount of a drug or pharmacologically active agent will vary depending on the route of administration, the selected compound, and the species to which the drug or pharmacologically active agent is administered. It is also recognized that one of skill in the art will determine appropriate effective amounts by taking into account such factors as metabolism, bioavailability, and other factors that affect plasma levels of a drug or pharmacologically active agent following administration within the unit dose ranges disclosed further herein for different routes of administration.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active") as in a "pharmacologically active" derivative or metabolite, refers to a derivative or metabolite having the same type of pharmacological activity as the parent compound. When the term "pharmaceutically acceptable" is used to refer to a derivative (e.g., a salt or an analog) of an active agent, it is to be understood that the compound is pharmacologically active as well, i.e., therapeutically effective for treating non-inflammatory GI tract disorders.

By "continuous" dosing is meant the chronic administration of a selected active agent. By "as-needed" dosing, also known as "pro re nata" "prn" dosing, and "on demand" dosing or administration is meant the administration of a single dose of the active agent at some time prior to commencement of an activity wherein suppression of the symptoms of a non-inflammatory GI tract disorder, would be desirable. Administration can be immediately prior to such an activity, including about 0 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, or about 10 hours prior to such an activity, depending on the formulation.

By "short-term" is intended any period of time up to and including about 8 hours, about 7 hours, about 6 hours, about 5 hours, about 4 hours, about 3 hours, about 2 hours, about 1 hour, about 40 minutes, about 20 minutes, or about 10 minutes after drug administration.

By "rapid-offset" is intended any period of time up to and including about 8 hours, about 7 hours, about 6 hours, about 5 hours, about 4 hours, about 3 hours, about 2 hours, about 1 hour, about 40 minutes, about 20 minutes, or about 10 minutes after drug administration.

The term "controlled release" is intended to refer to any drug-containing formulation in which release of the drug is not immediate, i.e., with a "controlled release" formulation, oral administration does not result in immediate release of the drug into an absorption pool. The term is used interchangeably with "non-immediate release" as defined in Remington: The Science and Practice of Pharmacy, Twentieth Ed. (Philadelphia, Pa.: Lippincott Williams & Wilkins, 2000).

The "absorption pool" represents a solution of the drug administered at a particular absorption site, and $k_r$, $k_a$, and $k_e$ are first-order rate constants for: 1) release of the drug from the formulation; 2) absorption; and 3) elimination, respectively. For immediate release dosage forms, the rate constant for drug release $k_r$ is far greater than the absorption rate constant $k_a$. For controlled release formulations, the opposite is true, i.e., $k_r <<< k_a$, such that the rate of release of drug from the dosage form is the rate-limiting step in the delivery of the drug to the target area. The term "controlled release" as used herein includes any nonimmediate release formulation, including but not limited to sustained release, delayed release and pulsatile release formulations.

The term "sustained release" is used in its conventional sense to refer to a drug formulation that provides for gradual release of a drug over an extended period of time, and that preferably, although not necessarily, results in substantially constant blood levels of a drug over an extended time period such as up to about 72 hours, about 66 hours, about 60 hours, about 54 hours, about 48 hours, about 42 hours, about 36 hours, about 30 hours, about 24 hours, about 18 hours, about 12 hours, about 10 hours, about 8 hours, about 7 hours, about 6 hours, about 5 hours, about 4 hours, about 3 hours, about 2 hours, or about 1 hour after drug administration.

The term "delayed release" is used in its conventional sense to refer to a drug formulation that provides for an initial release of the drug after some delay following drug administration and that preferably, although not necessarily, includes a delay of up to about 10 minutes, about 20 minutes, about 30 minutes, about 1 hour, about 2 hours, about 3 hours, about 4 hours, about 5 hours, about 6 hours, about 7 hours, about 8 hours, about 9 hours, about 10 hours, about 11 hours, or about 12 hours.

The term "pulsatile release" is used in its conventional sense to refer to a drug formulation that provides release of the drug in such a way as to produce pulsed plasma profiles of the drug after drug administration. The term "immediate release" is used in its conventional sense to refer to a drug formulation that provides for release of the drug immediately after drug administration.

By the term "transdermal" drug delivery is meant delivery by passage of a drug through the skin or mucosal tissue and into the bloodstream.

The term "topical administration" is used in its conventional sense to mean delivery of a topical drug or pharmacologically active agent to the skin or mucosa.

The term "oral administration" is used in its conventional sense to mean delivery of a drug through the mouth and ingestion through the stomach and digestive tract.

The term "inhalation administration" is used in its conventional sense to mean delivery of an aerosolized form of the drug by passage through the nose or mouth during inhalation and passage of the drug through the walls of the lungs.

By the term "parenteral" drug delivery is meant delivery by passage of a drug into the blood stream without first having to pass through the alimentary canal, or digestive tract. Parenteral drug delivery may be "subcutaneous," referring to delivery of a drug by administration under the skin. Another form of parenteral drug delivery is "intramuscular," referring to delivery of a drug by administration into muscle tissue. Another form of parenteral drug delivery is "intradermal," referring to delivery of a drug by administration into the skin. An additional form of parenteral drug delivery is "intravenous," referring to delivery of a drug by administration into a vein. An additional form of parenteral drug delivery is "intra-arterial," referring to delivery of a drug by administration into an artery. Another form of parenteral drug delivery is "transdermal," referring to delivery of a drug by passage of the drug through the skin and into the bloodstream.

Still another form of parenteral drug delivery is "transmucosal," referring to administration of a drug to the mucosal surface of an individual so that the drug passes through the mucosal tissue and into the individual's blood stream. Transmucosal drug delivery may be "buccal" or "transbuccal," referring to delivery of a drug by passage through an individual's buccal mucosa and into the bloodstream. Another form of transmucosal drug delivery herein is "lingual" drug delivery, which refers to delivery of a drug by passage of a drug through an individual's lingual mucosa and into the bloodstream. Another form of transmucosal drug delivery herein is "sublingual" drug delivery, which refers to delivery of a drug by passage of a drug through an individual's sublingual mucosa and into the bloodstream. Another form of transmucosal drug delivery is "nasal" or "intranasal" drug delivery, referring to delivery of a drug through an individual's nasal mucosa and into the bloodstream. An additional form of transmucosal drug delivery herein is "rectal" or "transrectal" drug delivery, referring to delivery of a drug by passage of a drug through an individual's rectal mucosa and into the bloodstream. Another form of transmucosal drug delivery is "urethral" or "transurethral" delivery, referring to delivery of the drug into the urethra such that the drug contacts and passes through the wall of the urethra. An additional form of transmucosal drug delivery is "vaginal" or "transvaginal" delivery, referring to delivery of a drug by passage of a drug through an individual's vaginal mucosa and into the bloodstream. An additional form of transmucosal drug delivery is "perivaginal" delivery, referring to delivery of a drug through the vaginolabial tissue into the bloodstream.

In order to carry out the method of the invention, a selected active agent is administered to a patient suffering from a non-inflammatory GI tract disorder. A therapeutically effective amount of the active agent may be administered orally, intravenously, subcutaneously, transmucosally (including buccally, sublingually, transurethrally, and rectally), topically, transdermally, by inhalation, intrathecally, or using any other route of administration.

GI Tract Disorders

GI tract disorders affect the quality of life of millions of men and women in the United States every year. GI tract disorders may involve disturbances of the GI smooth muscle, epithelium, sensory afferent neurons, or central nervous system pathways. In spite of the uncertainty regarding whether central or peripheral mechanisms, or both, are involved in GI tract disorders, many proposed mechanisms implicate neurons and pathways that mediate visceral sensation. Viscerosensory information from the GI tract is relayed by sensory fibers that enter the spinal cord via the dorsal root ganglion (DRG) or project to the nodose ganglion via vagal afferents (*Physiology*, ed. R. M Berne and M. N. Levy, 1983, CV Mosby Co. St. Louis). A number of different subtypes of sensory afferent neurons may be involved in neurotransmission from the GI tract. These may be classified as, but not limited to, small diameter, medium diameter, large diameter, myelinated, unmyelinated, sacral, lumbar, DRG, vagal, nodose, peptidergic, non-peptidergic, IB4 positive, IB4 negative, C fiber, Aδ fiber, Aβ fiber, high threshold or low threshold neurons.

Structural and Non-Structural GI Tract Disorders

GI tract disorders have been characterized as structural (or mucosal) GI tract disorders and non-structural (or non-mucosal) GI tract disorders. Structural disorders include inflammatory bowel disorders and non-inflammatory structural GI tract disorders. Non-structural disorders include a variety of disorders classified as functional GI tract disorders.

Inflammatory bowel disorders include a group of disorders that can cause inflammation or ulceration of the GI tract. Ulcerative colitis and Crohn's disease are the most common types of inflammatory bowel disorders, although collagenous colitis, lymphocytic (microscopic) colitis, and other disorders have also been described.

Ulcerative colitis is a chronic inflammatory disorder of unknown etiology afflicting the large intestine and, except when very severe, is limited to the bowel mucosa. The course of this disorder may be continuous or relapsing and may be mild or severe. Medical treatment primarily includes the use of salicylate derivatives, glucocorticosteroids such as prednisone or prednisone acetate and anti-metabolites dependent on the clinical state of the patient. Salicylate derivatives, such as sulphazine or mesalamine, are efficacious in patients with mild cases of the disorder. Glucocorticosteroids and anti-metabolites are efficacious in patients with moderate or severe disease but are associated with a number of side effects. Patients who need chronic doses of glucocorticosteroids or anti-metabolites for control of their disorder eventually undergo removal of the colon surgically to eliminate the disease.

Like ulcerative colitis, Crohn's disease (also known as regional enteritis, ileitis, or granulomatous ileocolitis) is a chronic inflammatory disorder of unknown etiology; however the location and pathology of the disease differ. Crohn's disease typically presents in either the small intestine, large intestine or the combination of the two locations and can cause inflammation deeper into the muscle and serosa located within the intestinal wall. The course of the disorder may be continuous or relapsing and may be mild or severe. Medical treatment includes the continuous use of salicylate derivatives, glucocorticosteroids, anti-metabolites, and administration of an anti-TNF antibody. Many Crohn's disease patients require intestinal surgery for a problem related to the disease, but unlike ulcerative colitis subsequent relapse is common.

Collagenous colitis and lymphocytic colitis are idiopathic inflammatory disorders of the colon that cause watery diarrhea typically in middle-aged or older individuals. Lymphocytic colitis is distinguished from collagenous colitis by the absence of a thickened subepithelial collagenous layer. Bismuth in the form of Pepto-Bismol may be an effective treatment in some patients, although more severe cases may require the use of salicylate derivatives, antibiotics such as metronidazole, and glucocorticosteroids.

Functional GI tract disorders are characterized by presentation of abdominal-type symptoms without evidence of changes in metabolism or structural abnormalities. Disorders that are typically considered under functional disorders include dysphagia, non-ulcer dyspepsia, irritable bowel syndrome, slow-transit constipation, and evacuation disorders (Camilleri (2002) Gastrointestinal Motility Disorders, In *WebMD Scientific American Medicine*, edited by David C. Dale and Daniel D. Federman, New York, N.Y., WebMD). A prominent example of a functional GI tract disorder is irritable bowel syndrome (IBS), also known by a variety of synonyms, including functional bowel, pylorospasm, nervous indigestion, spastic colon, spastic colitis, spastic bowel, intestinal neurosis, functional colitis, irritable colon, mucous colitis, laxative colitis, and functional dyspepsia. IBS generally leads to abdominal pain and/or discomfort and an alteration in bowel habit with no clear etiology. Diagnosis relies on Rome criteria taking into account all symptoms related to patient presentation. (See, e.g., Drossman et al. (1997) *Gastroenterology*, 112: 2120). Patients typically present with symptoms consistent with hyperalgesia and allodynia.

At present, treatments for IBS have been largely ineffective, and have included stress management, diet, and drugs. Psychoactive drugs, such as anxiolytics and antidepressants, have been utilized but have limited utility because of the side effect profile. Antispasmodics and various antidiarrheal preparations have also been used but these remain as unsatisfactory remedies to patients with IBS.

Non-ulcer dyspepsia (NUD) is another prominent example of a functional GI tract disorder with no established etiology. Symptoms related to NUD include nausea, vomiting, pain, early satiety, bloating and loss of appetite. Altered gastric emptying and increased gastric sensitivity and distress may contribute to NUD but do not completely explain its presentation. Treatments include behavioral therapy, psychotherapy, or administration of antidepressants, motility regulatory agents, antacids, H$_2$-receptor antagonists, and, prokinetics. However, many of these treatments have shown limited efficacy in many patients.

Anatomical and Physiological Distinctions

In addition to the structural/non-structural classification described above, GI tract disorders may also be sub-classified based upon anatomical, physiological, and other characteristics of different portions of the GI tract as described in Sleisenger and Fordtran's Gastrointestinal and Liver Disease, 6$^{th}$ Ed. (W.B. Saunders Co. 1998); K. M. Sanders (1 996) *Gastroenterology*, 111: 492–515; P. Holzer (1998) *Gastroenterology*, 114: 823–839; and R. K. Montgomery et al. (1999) *Gastroenterology*, 116: 702–731. For example, acid peptic disorders are generally thought to arise from damage due to acidic and/or peptic activity of gastric secretions and may affect the esophagus, stomach, and duodenum. Acid peptic disorders include gastroesophageal reflux disease, peptic ulcers (both gastric and duodenal), erosive esophagitis and esophageal stricture. Zollinger-Ellison Syndrome may be considered an acid peptic disorder since it typically presents with multiple ulcers due to excessive acid secretion caused by a endocrine tumor. Treatments typically include gastric acid suppressive therapies, antibiotics, and surgery. In some patients, however, these therapies have proven ineffective.

Another sub-classification for GI tract disorders may be drawn between gastroesophageal and intestinal disorders based upon characteristics between different portions of the GI tract as disclosed in Sleisenger and Fordtran's Gastrointestinal and Liver Disease, 6$^{th}$ Ed. (W.B. Saunders Co. 1998); K. M. Sanders (1996) *Gastroenterology*, 111: 492–515; P. Holzer (1998) *Gastroenterology*, 114: 823–839; and R. K. Montgomery et al. (1999) *Gastroenterology*, 116: 702–731. Structural gastroesophageal disorders include disorders of the stomach and/or esophagus where there is no evidence of structural perturbations (including those observed in the mucosa) distal to the pylorus. Dyspepsia (chronic pain or discomfort centered in the upper abdomen) is a prominent feature of most structural gastroesophageal disorders but can also be observed in non-structural perturbations, and has been estimated to account for 2 to 5 percent of all general practice consultations. Structural gastroesophageal disorders include gastritis and gastric cancer. By contrast, structural intestinal tract disorders occur in both the small intestine (the duodenum, jejunum, and ileum) and in the large intestine. Structural intestinal tract disorders are characterized by structural changes in the mucosa or in the muscle layers of the intestine, and include non-peptic ulcers of the small intestine, malignancies, and diverticulosis. Non-peptic ulcers in the small intestine are typically related to administration of non-steroidal anti-inflammatory drugs. Diverticulosis is a disorder that rarely occurs in the small intestine and most commonly appears in the colon.

Non-Inflammatory GI Tract Disorders

Non-inflammatory GI tract disorders include non-inflammatory structural GI tract disorders and non-structural GI tract disorders. Non-inflammatory structural GI tract disorders include, but are not limited to, hiatal hernias, strictures, esophageal webs, Schatzki's ring, esophageal diverticula, and esophageal scleroderma. Non-structural GI tract disorders include motor disorders of the esophagus such as achalasia and diffuse esophageal spasm, and functional GI tract disorders such as irritable bowel syndrome.

Hiatal (also called hiatus) hernias may be divided into two types: sliding and paraesophageal. (*First Principles of Gastroenterology, The basis of disease and an approach to management* (2000), 4$^{th}$ edition, Thompson ABR and Shaffer EA, eds., Canadian Association of Gastroenterology and AstraZeneca). A sliding hiatal hernia is relatively common and occurs where a circumferential cuff of cardia and proximal stomach migrates into the thorax through the diaphragmatic hiatus. (See, e.g., Thompson and Shaffer, *First Principles of Gastroenterology*, supra). The etiology of sliding hiatal hernias is unclear, and they often reduce and reform spontaneously, although surgical correction may be performed in extreme cases. (See, e.g., Thompson and Shaffer, *First Principles of Gastroenterology*, supra). By contrast, paraesophageal hiatal hernias are relatively uncommon and occur where the fundus of the stomach migrates through the hiatus alongside the esophagus without any displacement of the gastroesophageal junction. (See, e.g., Thompson and Shaffer, *First Principles of Gastroenterology*, supra). The etiology of paraesophageal hiatal hernias is also unclear. Paraesophageal hiatal hernias are often asymptomatic, but many are treated surgically because the herniated portion may become strangulated and infarcted. (See, e.g., Thompson and Shaffer, *First Principles of Gastroenterology*, supra).

A stricture is a narrowing of the GI tract. An esophageal stricture is a narrowing of the esophagus.

Esophageal webs are thin, membrane-like structures that project into the esophageal lumen, are covered on both sides with squamous epithelium, and are most commonly found in the cervical esophagus. (See, e.g., Thompson and Shaffer, *First Principles of Gastroenterology*, supra). Esophageal webs rarely occlude enough of the esophageal lumen to cause dysphagia and are usually detected incidentally during barium x-rays. (See, e.g., Thompson and Shaffer, *First Principles of Gastroenterology*, supra). Although some esophageal webs may be congenital in origin, others may form after esophageal injury. (See, e.g., Thompson and Shaffer, *First Principles of Gastroenterology*, supra). The precise etiology of esophageal webs is unclear. (See, e.g., Thompson and Shaffer, *First Principles of Gastroenterology*, supra).

Like esophageal webs, Schatzki's ring is also a membrane-like structure. (See, e.g., Thompson and Shaffer, *First Principles of Gastroenterology*, supra). Unlike webs, however, Schatzki's ring is lined by squamous epithelium on its superior aspect and columnar epithelium inferiorly. (See, e.g., Thompson and Shaffer, *First Principles of Gastroenterology*, supra). Schatzki's ring rarely occludes enough of the esophageal lumen to cause dysphagia, but are detected incidentally in up to 10% of all upper GI barium x-rays. (See, e.g., Thompson and Shaffer, *First Principles of Gastroenterology*, supra). Where dysphagia occurs, however, Schatzki's ring is a common cause. (See, e.g., Thompson and Shaffer, *First Principles of Gastroenterology*, supra). Treatment of symptomatic Schatzki's ring involves shattering the ring with a large-diameter bougie or a balloon dilator. (See, e.g., Thompson and Shaffer, *First Principles of Gastroenterology*, supra).

Esophageal diverticula are outpouchings of one or more layers of the esophageal wall, and include midesophageal and lower esophageal diverticula.

Midesophageal diverticula (also called "traction" diverticula) were once thought to arise secondary to old mediastinal inflammation, such as tuberculosis, that caused adherence of mediastinal structures to the outer esophageal wall. (See, e.g., Thompson and Shaffer, *First Principles of Gastroenterology*, supra). Recent evidence suggests that very few midesophageal diverticula arise this way, but are instead associated with a motility disorder. (See, e.g., Thompson and Shaffer, *First Principles of Gastroenterology*, supra). In fact, it is likely that midesophageal diverticula are actually "pulsion" diverticula formed when a peristaltic wave deteriorates into a simultaneous or spastic contraction in the smooth-muscle esophagus. (See, e.g., Thompson and Shaffer, *First Principles of Gastroenterology*, supra). Midesophageal diverticula rarely require specific therapy, although the associated motor disorder may require treatment if symptomatic. (See, e.g., Thompson and Shaffer, *First Principles of Gastroenterology*, supra).

Lower esophageal diverticula are also "pulsion" diverticula, and form just above the lower esophageal sphincter. (See, e.g., Thompson and Shaffer, *First Principles of Gastroenterology*, supra). Lower esophageal diverticula are invariably associated with an esophageal motor disorder, and patients usually present with dysphagia and/or angina-like chest pain. (See, e.g., Thompson and Shaffer, *First Principles of Gastroenterology*, supra). Patients may also complain of nocturnal regurgitation of large quantities of stagnant fluid. (See, e.g., Thompson and Shaffer, *First Principles of Gastroenterology*, supra). Current treatment options include the use of nitrates and some L-type calcium channel blockers, although esophageal myotomy may be an option for patients with severe disease unresponsive to medical measures. (See, e.g., Thompson and Shaffer, *First Principles of Gastroenterology*, supra).

Esophageal scleroderma often occurs in patients with general scleroderma, and may be present even in the absence of obvious skin and joint involvement. (See, e.g., Thompson and Shaffer, *First Principles of Gastroenterology*, supra). Initial damage involves small blood vessels, which leads to intramural neuronal dysfunction and ultimately to actual muscle damage and fibrosis. (See, e.g., Thompson and Shaffer, *First Principles of Gastroenterology*, supra). These effects produce a very hypotensive lower esophageal sphincter and weak non-propulsive esophageal contractions. (See, e.g., Thompson and Shaffer, *First Principles of Gastroenterology*, supra). Scleroderma may also involve the stomach and cause delayed gastric emptying as well as gastroesophageal reflux. (See, e.g., Thompson and Shaffer, *First Principles of Gastroenterology*, supra). Patients may report dysphagia, which can be due to poor esophageal propulsion and/or reflux-induced stricture. (See, e.g., Thompson and Shaffer, *First Principles of Gastroenterology*, supra). Such patients need very aggressive treatment for gastroesophageal reflux, but because of very poor peristaltic function, anti-reflux surgery may markedly worsen the dysphagia by increasing the barrier at the lower esophageal sphincter. (See, e.g., Thompson and Shaffer, *First Principles of Gastroenterology*, supra).

Motor disorders of the esophagus may be classified as primary or secondary. Primary motor disorders of the esophagus usually affect the esophagus alone and have no known etiology. (See, e.g., Thompson and Shaffer, *First Principles of Gastroenterology*, supra). By contrast, secondary motor disorders of the esophagus are motility disturbances caused by some other systemic or local condition, including acid-reflux-induced dysmotility and dysmotility related to diabetic neuropathy. (See, e.g., Thompson and Shaffer, *First Principles of Gastroenterology*, supra).

Primary motor disorders of the esophagus include diffuse esophageal spasm (DES) and achalasia. (See, e.g., Thompson and Shaffer, *First Principles of Gastroenterology*, supra). DES is characterized by normal peristalsis interrupted by frequent high-pressure non-propagated (or "tertiary") waves as well as multi-peaked waves, with patients often presenting with dysphagia and chest pain. (See, e.g., Thompson and Shaffer, *First Principles of Gastroenterology*, supra). In advanced DES, an x-ray examination shows a corkscrew pattern due to different portions of the esophagus vigorously and simultaneously contracting. (See, e.g., Thompson and Shaffer, *First Principles of Gastroenterology*, supra). Although unknown, the etiology of DES may relate to degenerative changes in the intrinsic and extrinsic esophageal nerves. (See, e.g., Thompson and Shaffer, *First Principles of Gastroenterology*, supra). Current treatment options include the use of nitrates and some L-type calcium channel blockers, although long esophageal myotomy may be an option for patients with severe disease unresponsive to medical measures. (See, e.g., Thompson and Shaffer, *First Principles of Gastroenterology*, supra).

Achalasia is a relatively uncommon primary motility disorder characterized by aperistalsis in the body of the esophagus, an elevated lower esophageal sphincter pressure, and absent or incomplete lower esophageal sphincter relaxation in response to swallowing. (See, e.g., Thompson and Shaffer, *First Principles of Gastroenterology*, supra). The absence of lower esophageal sphincter relaxation produces progressive proximal dilation of the esophagus and elevated resting intraesophageal pressure. (See, e.g., Thompson and Shaffer, *First Principles of Gastroenterology*, supra). The esophagus is dilated on x-ray examination and the distal esophagus narrows in a beak-like fashion. Achalasia is caused by degeneration of inhibitory neurons within the esophageal and lower esophageal sphincter myenteric plexus, as well as nerve damage in the vagal nerve trunks and the dorsal motor nuclei. (See, e.g., Thompson and Shaffer, *First Principles of Gastroenterology*, supra). The parasite Trypanosoma cruzi can cause achalasia by destroying myenteric neurons (Chagas' disease). (See, e.g., Thompson and Shaffer, *First Principles of Gastroenterology*, supra). Neoplastic disease can also cause "secondary" achalasia by interfering with esophageal and lower esophageal sphincter nerve function. (See, e.g., Thompson and Shaffer, *First Principles of Gastroenterology*, supra).

Patients with achalasia often present with dysphagia, and some patients may complain of chest pain and/or regurgitation of esophageal contents. (See, e.g., Thompson and Shaffer, *First Principles of Gastroenterology*, supra). Heartburn may also occur, although it is caused by lactic acid formed by fermentation of stagnant esophageal contents and not from gastroesophageal reflux. (See, e.g., Thompson and Shaffer, *First Principles of Gastroenterology*, supra). Current treatment options include the use of nitrates and some L-type calcium channel blockers. (See, e.g., Thompson and Shaffer, *First Principles of Gastroenterology*, supra). Pneumatic balloon dilation of the lower esophageal sphincter may also be used, which consists of passing a balloon across the sphincter and inflating it rapidly so that the sphincter is forcefully dilated. (See, e.g., Thompson and Shaffer, *First Principles of Gastroenterology*, supra). For patients who do not respond to pneumatic dilation, a Heller myotomy may be used in which a longitudinal incision is made through the muscle of the lower esophageal sphincter. (See, e.g., Thompson and Shaffer, *First Principles of Gastroenterology*, supra). Some recent studies have also found that injection of botulinum toxin into the muscle of the lower esophageal sphincter can alleviate dysphagia in approximately two-thirds of patients with achalasia, but the average duration of relief is only one year. (See, e.g., Thompson and Shaffer, *First Principles of Gastroenterology*, supra).

As disclosed further herein, functional GI tract disorders are characterized by presentation of abdominal-type symptoms without evidence of changes in metabolism or structural abnormalities. As described more fully elsewhere herein, disorders that are typically considered under functional disorders include dysphagia, non-ulcer dyspepsia, irritable bowel syndrome, slow-transit constipation, and evacuation disorders.

Peripheral vs. Central Effects

The mammalian nervous system comprises a central nervous system (CNS, comprising the brain and spinal cord) and a peripheral nervous system (PNS, comprising sympathetic, parasympathetic, sensory, motor, and enteric neurons outside of the brain and spinal cord). Where an active agent according to the present invention is intended to act centrally (i.e., exert its effects via action on neurons in the CNS), the active agent must either be administered directly into the CNS or be capable of bypassing or crossing the blood-brain barrier. The blood-brain barrier is a capillary wall structure that effectively screens out all but selected categories of substances present in the blood, preventing their passage into the CNS. The unique morphologic characteristics of the brain capillaries that make up the blood-brain barrier are: 1) epithelial-like high resistance tight junctions which literally cement all endothelia of brain capillaries together within the blood-brain barrier regions of the CNS; and 2) scanty pinocytosis or transendothelial channels, which are abundant in endothelia of peripheral organs. Due to the unique characteristics of the blood-brain barrier, hydrophilic drugs and peptides that readily gain access to other tissues in the body are barred from entry into the brain or their rates of entry are very low.

The blood-brain barrier can be bypassed effectively by direct infusion of the active agent into the brain, or by intranasal administration or inhalation of formulations suitable for uptake and retrograde transport of the active agent by olfactory neurons. The most common procedure for administration directly into the CNS is the implantation of a catheter into the ventricular system or intrathecal space. Alternatively, the active agent can be modified to enhance its transport across the blood-brain barrier. This generally requires some solubility of the drug in lipids, or other appropriate modification known to one of skill in the art. For example, the active agent may be truncated, derivatized, latentiated (converted from a hydrophilic drug into a lipid-soluble drug), conjugated to a lipophilic moiety or to a substance that is actively transported across the blood-brain barrier, or modified using standard means known to those skilled in the art. See, for example, Pardridge, Endocrine Reviews 7: 314–330 (1986) and U.S. Pat. No. 4,801,575.

Where an active agent according to the present invention is intended to act exclusively peripherally (i.e., exert its effects via action either on neurons in the PNS or directly on target tissues), it may be desirable to modify the compounds of the present invention such that they will not pass the blood-brain barrier. The principle of blood-brain barrier permeability can therefore be used to design active agents with selective potency for peripheral targets. Generally, a lipid-insoluble drug will not cross the blood-brain barrier, and will not produce effects on the CNS. A basic drug that acts on the nervous system may be altered to produce a selective peripheral effect by quarternization of the drug, which decreases its lipid solubility and makes it virtually unavailable for transfer to the CNS. For example, the charged antimuscarinic drug methscopalamine bromide has peripheral effects while the uncharged antimuscarinic drug scopolamine acts centrally. One of skill in the art can select and modify active agents of the present invention using well-known standard chemical synthetic techniques to add a lipid impermeable functional group such a quaternary amine, sulfate, carboxylate, phosphate, or sulfonium to prevent transport across the blood-brain barrier. Such modifications are by no means the only way in which active agents of the present invention may be modified to be impermeable to the blood-brain barrier; other well known pharmaceutical techniques exist and would be considered to fall within the scope of the present invention.

Agents

Compounds useful in the present invention include any active agent as defined elsewhere herein. Such active agents include, for example, any compound that binds to the Cav2.2 subunit of a calcium channel.

Voltage gated calcium channels, also known as voltage dependent calcium channels, are multi-subunit membrane-spanning proteins which permit controlled calcium influx from an extracellular environment into the interior of a cell. Opening and closing (gating) of voltage gated calcium channels is controlled by a voltage sensitive region of the protein containing charged amino acids that move within an electric field. The movement of these charged groups leads to conformational changes in the structure of the channel resulting in conducting (open/activated) or non-conducting (closed/inactivated) states.

Voltage gated calcium channels are present in a variety of tissues and are implicated in several vital processes in animals. Changes in calcium influx into cells mediated through these calcium channels have been implicated in various human diseases such as epilepsy, stroke, brain trauma, Alzheimer's disease, multi-infarct dementia, other classes of dementia, Korsakoff's disease, neuropathy caused by a viral infection of the brain or spinal cord (e.g., human immunodeficiency viruses, etc.), amyotrophic lateral sclerosis, convulsions, seizures, Huntington's disease, amnesia, or damage to the nervous system resulting from reduced oxygen supply, poison, or other toxic substances (See, e.g., U.S. Pat. No. 5,312,928).

Voltage gated calcium channels have been classified by their electrophysiological and pharmacological properties as T, L, N, P and Q types (for reviews see McCleskey et al. (1991) Curr. Topics Membr. 39:295–326; and Dunlap et al. (1995) Trends. Neurosci. 18:89–98). Because there is some overlap in the biophysical properties of the high voltage-activated channels, pharmacological profiles are useful to further distinguish them. L-type channels are sensitive to dihydropyridine agonists and antagonists. N-type channels are blocked by the peptides ω-conotoxin GVIA and ω-conotoxin MVIIA, peptide toxins from the cone shell mollusks, *Conus geographus* and *Conus magus*, respectively. P-type channels are blocked by the peptide ω-agatoxin IVA from the venom of the funnel web spider, *Agelenopsis aperta*, although some studies have suggested that ω-agatoxin IVA also blocks N-type channels (Sidach at al. (2000) *J. Neurosci*. 20: 7174–82). A fourth type of high voltage-activated calcium channel (Q-type) has been described, although whether the Q- and P-type channels are distinct molecular entities is controversial (Sather et al.(1995) *Neuron* 11:291–303; Stea et al. (1994) *Proc. Natl. Acad. Sci. USA* 91:10576–10580; Bourinet et al. (1999) *Nature Neuroscience* 2:407–415).

Different types of calcium channels are primarily defined by different subunits that may be divided into three structurally and functionally related families: $Ca_v1$, $Ca_v2$, and $Ca_v3$ (for reviews, see Caterall (2000) *Annu. Rev. Cell. Dev. Biol*. 16: 521–55; Ertel et al. (2000) *Neuron* 25: 533–55). L-type currents are mediated by a $Ca_v1$ family of $α_1$ subunits (see Caterall, *Annu. Rev. Cell. Dev. Biol*., supra). $Ca_v2$ channels form a distinct family with less than 40% amino acid sequence identity with $Ca_v1α_1$ subunits (see Caterall, *Annu. Rev. Cell. Dev. Biol*., supra). Cloned $Ca_v2.1$ subunits conduct P- or Q-type currents that are inhibited by ω-agatoxin IVA (see Caterall, *Annu. Rev. Cell. Dev. Biol*., supra; Sather et al. (1993) *Neuron* 11: 291–303; Stea et al. (1994) *Proc. Natl. Acad. Sci. USA* 91: 10576–80; Bourinet et al. (1999) *Nat. Neurosci*. 2: 407–15). $Ca_v2.2$ subunits conduct N-type calcium currents and have a high affinity for ω-conotoxin GVIA, ω-conotoxin MVIIA, and synthetic versions of these peptides including Ziconotide (SNX-111) (see Caterall, *Annu. Rev. Cell. Dev. Biol*., supra; Dubel et al. (1992) *Proc. Natl. Acad. Sci. USA* 89:5058–62; Williams et al. (1992) *Science* 257: 389–95). Cloned $Ca_v2.3$ subunits conduct a calcium current known as R-type and are resistant to organic antagonists specific for L-type calcium currents and peptide toxins specific for N-type or P/Q-type currents ((see Caterall, *Annu. Rev. Cell. Dev. Biol*., supra; Randall et al. (1995) *J. Neurosci*. 15: 2995–3012; Soong et al. (1994) *Science* 260: 1133–36; Zhang et al. (1993) *Neuropharmacology* 32: 1075–88).

Agents useful in the practice of the invention include, but are not limited to:

a. ω-conotoxin GVIA or a salt, enantiomer, analog, ester, amide, prodrug, active metabolite, or derivative thereof;

b. ω-conotoxin MVIIA or a salt, enantiomer, analog, ester, amide, prodrug, active metabolite, or derivative thereof;

c. ω-conotoxin CNVIIA or a salt, enantiomer, analog, ester, amide, prodrug, active metabolite, or derivative thereof;

d. ω-conotoxin CVIID or a salt, enantiomer, analog, ester, amide, prodrug, active metabolite, or derivative thereof;

e. ω-conotoxin AM336 or a salt, enantiomer, analog, ester, amide, prodrug, active metabolite, or derivative thereof;

f. Cilnidipine or a salt, enantiomer, analog, ester, amide, prodrug, active metabolite, or derivative thereof;

g. Amlodipine or a salt, enantiomer, analog, ester, amide, prodrug, active metabolite, or derivative thereof;

h. L-cysteine derivative 2A or a salt, enantiomer, analog, ester, amide, prodrug, active metabolite, or derivative thereof;

i. ω-agatoxin IVA or a salt, enantiomer, analog, ester, amide, prodrug, active metabolite, or derivative thereof;

j. N,N-dialkyl-dipeptidylamines or a salt, enantiomer, analog, ester, amide, prodrug, active metabolite, or derivative thereof;

k. Levetiracetam or a salt, enantiomer, analog, ester, amide, prodrug, active metabolite, or derivative thereof; and l. Ziconotide (SNX-111) or a salt, enantiomer, analog, ester, amide, prodrug, active metabolite, or derivative thereof;

m. (S)-alpha-ethyl-2-oxo-1-pyrrolidineacetamide (illustrated below) and disclosed in U.S. Pat. Nos. 4,943,639, 4,837,223, and U.S. Pat. No. 4,696,943, or a salt, enantiomer, analog, ester, amide, prodrug, active metabolite, or derivative, thereof;

n. Substituted peptidylamines (illustrated below) as disclosed in PCT Publication No. WO 98/54123, or a salt, enantiomer, analog, ester, amide, prodrug, active metabolite, or derivative, thereof,

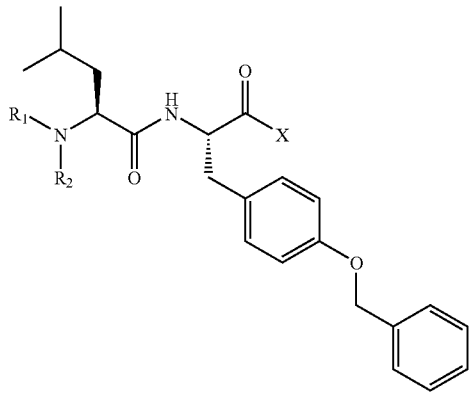

wherein X is selected from the group consisting of OR, $NR_1R_2$, and $COOR_1$, and $R_1$ and $R_2$ are selected from the group consisting of hydrogen and $C_1$–$C_8$ alkyl, aryl, and heteroaryl optimally substituted with one to three substituents;

o. PD-173212 (illustrated below), or a salt, enantiomer, analog, ester, amide, prodrug, active metabolite, or derivative, thereof;

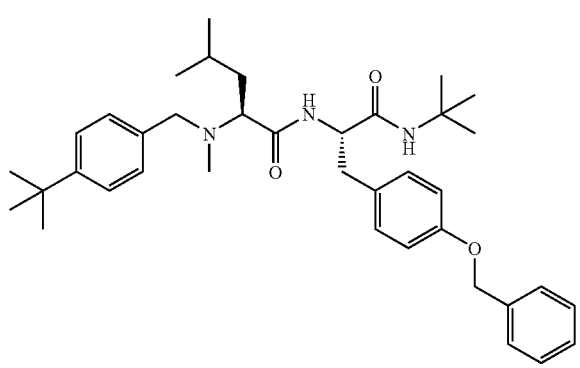

p. Reduced dipeptide analogues (illustrated below) as disclosed in U.S. Pat. No. 6,316,440 and PCT Publication No. WO 00/06559, or a salt, enantiomer, analog, ester, amide, prodrug, active metabolite, or derivative, thereof,

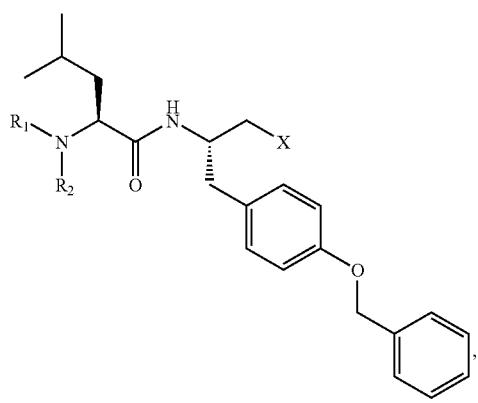

wherein X is selected from the group consisting of OR, $NR_1R_2$, and $COOR_1$, and $R_1$ and $R_2$ are selected from the group consisting of hydrogen and $C_1$–$C_8$ alkyl, aryl, and heteroaryl optimally substituted with one to three substituents, in particular, the two specific embodiments illustrated below;

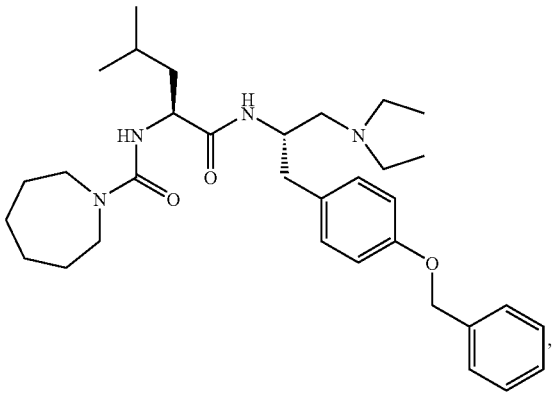

and

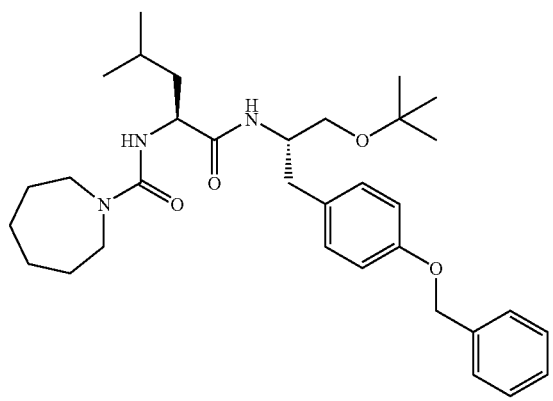

q. Amino acid derivatives (illustrated below) as disclosed in PCT Publication No. WO 99/02146, or a salt, enantiomer, analog, ester, amide, prodrug, active metabolite, or derivative, thereof,

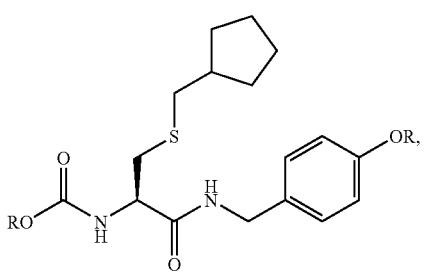

wherein R is selected from the group consisting of hydrogen and $C_1$–$C_6$ alkyl, aryl, and heteroaryl optimally substituted with one to three substituents, in particular, the specific embodiment illustrated below;

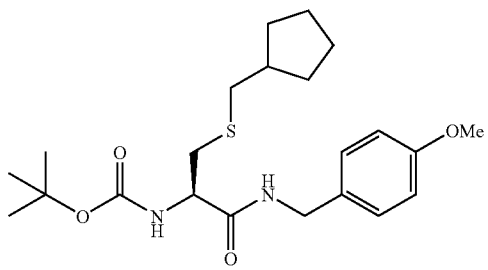

r. Benzazepine derivatives (illustrated below) as disclosed in Japanese Publication No. JP 2002363163, or a salt, enantiomer, analog, ester, amide, prodrug, active metabolite, or derivative, thereof,

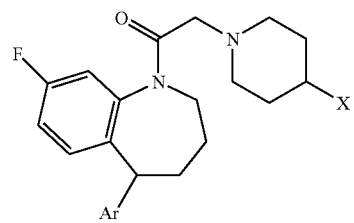

wherein Ar is selected from the group consisting of aryl and heteroaryl optimally substituted with one to three substituents, and X is selected from the group consisting of hydrogen and $C_1$–$C_6$ alkyl and alkoxy, in particular, the specific embodiment illustrated below;

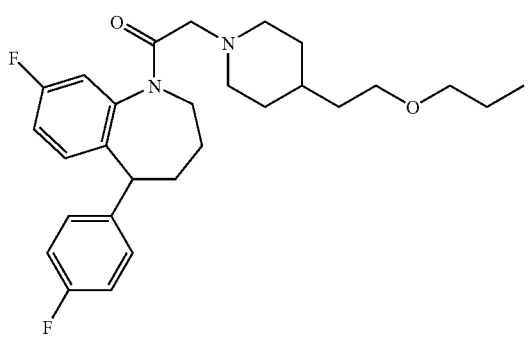

s. Compounds according to the structure illustrated below as disclosed in PCT Publication No. WO 02/36567, or a salt, enantiomer, analog, ester, amide, prodrug, active metabolite, or derivative, thereof,

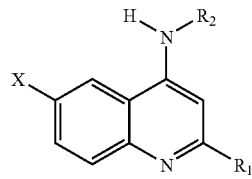

wherein X is selected from the group consisting of $R_1$ and $NHR_1$, $R_1$ is selected from the group consisting of hydrogen and $C_1$–$C_6$ alkyl, aryl, and heteroaryl optimally substituted with one to three substituents, and $R_2$ is $C_1$–$C_4$ alkyl or alkoxy, in particular, the two specific embodiments illustrated below;

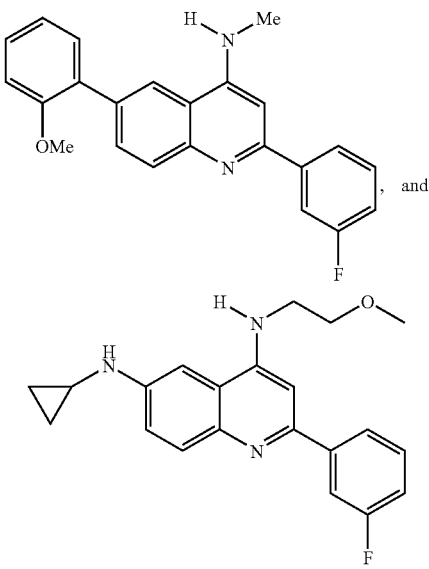

t. Compounds according to the structure illustrated below as disclosed in PCT Publication No. WO 03/018561, or a salt, enantiomer, analog, ester, amide, prodrug, active metabolite, or derivative, thereof,

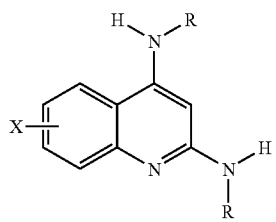

wherein X is selected from the group consisting of hydrogen and halogen, and R is selected from the group consisting of $C_1$–$C_6$ alkyl, aryl, and heteroaryl optimally substituted with one to three substituents, in particular, the two specific embodiments illustrated below;

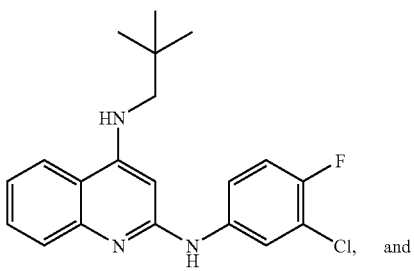

-continued

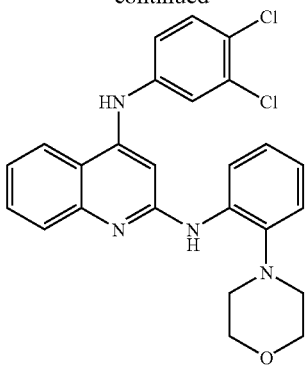

u. Compounds according to the structure illustrated below as disclosed in U.S. Patent Publication No. 2004009991 and PCT Publication No. WO 02/22588, or a salt, enantiomer, analog, ester, amide, prodrug, active metabolite, or derivative, thereof;

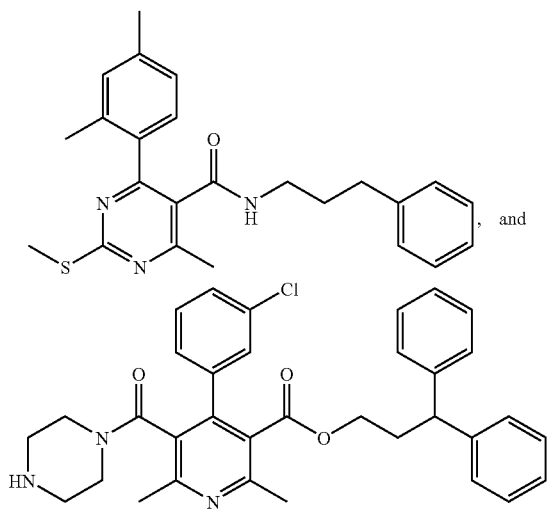

v. Dihydropyridine derivatives (illustrated below) as disclosed in U.S. Pat. No. 6,610,717, U.S. Patent Publication No. 2002193605, and PCT Publication No. WO 00/78720, or a salt, enantiomer, analog, ester, amide, prodrug, active metabolite, or derivative, thereof,

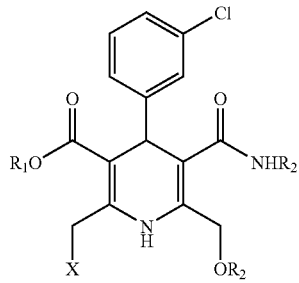

wherein X is selected from the group consisting of hydrogen and $C_1$–$C_4$ alkyl and alkoxy, $R_1$ is selected from the group consisting of hydrogen and $C_1$–$C_4$ alkyl, and $R_2$ is selected from the group consisting of $C_1$–$C_6$ alkyl, alkoxy, alkylamino, and aryl-substituted alkyl, in particular, the two specific embodiments illustrated below; and

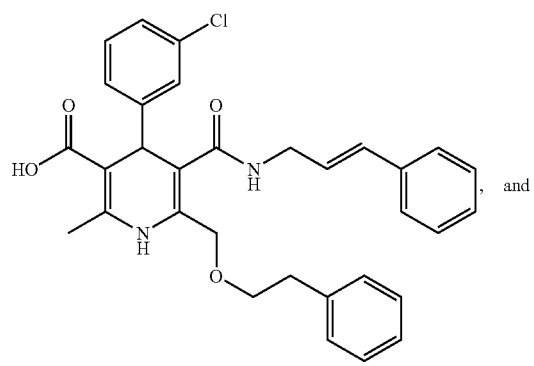

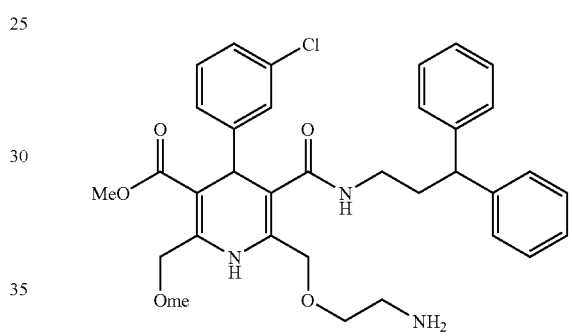

w. Diarylalkene and diarylalkane derivatives (illustrated below) as disclosed in PCT Publication No. WO 03/018538, or a salt, enantiomer, analog, ester, amide, prodrug, active metabolite, or derivative, thereof,

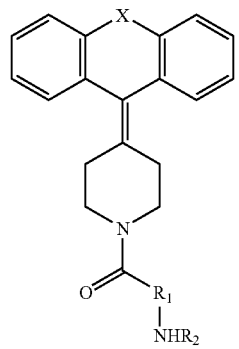

wherein X is selected from the group consisting of CHCH, $CH_2CH_2$, $CH_2$—Y, O, and S, Y is selected from the group consisting of O and S, $R_1$ is selected from the group consisting of $C_1$–$C_4$ alkyl and alkoxy, and $R_2$ is selected from the group consisting of hydrogen, $COOR_1$, and $C_1$–$C_4$ alkyl and alkoxy, in particular, the two specific embodiments illustrated below,

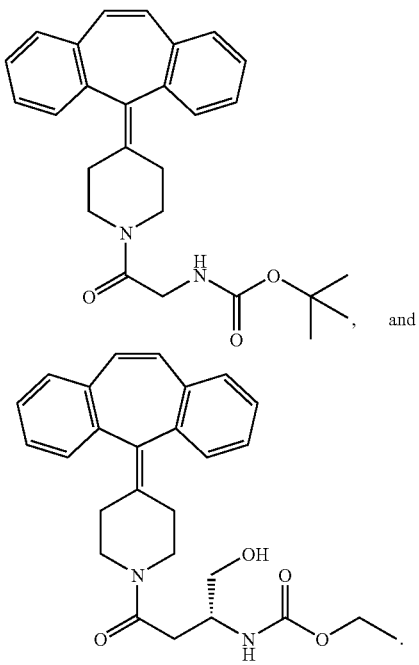

Such active agents also include other peptide, non-peptide, and peptidomimetic drug-like molecules that bind to Cav2.2-containing calcium channels as disclosed in Lewis et al. (2000) *J. Biol. Chem.* 10: 35335–44; Smith et al. (2002) *Pain* 96: 119–27; Takahara et al. (2002) *Eur. J. Pharmacol.* 434: 43–7; Favreau et al. (2001) *Biochemistry*, 40: 14567–575; Seko et al. (2001) *Bioorg. Med. Chem. Lett.* 11: 2067–70; Hu et al. (2000) *Bioorg. Med. Chem. Lett.* 8: 1203–12; Lew et al. (1997) *J. Biol. Chem.* 272: 12014–23. It is understood that the present invention also encompasses any pharmaceutically acceptable, pharmacologically active salts, enantiomers, analogs, esters, amides, prodrugs, active metabolites, and derivatives of the aforementioned compounds.

The identification of other agents that have affinity for the Cav2.2 subunit of a calcium channel and would be useful in the present invention can be determined by performing Cav2.2 subunit binding affinity, electrophysiolgic, and/or other screening methods as described in Kristipati et al. (*Mol. Cell. Neurosci.*, 5:219–228, 1994), Feng et al. (*J. Biol. Chem.*, 278: 20171–20178, 2003), Feng et al. (*J. Biol. Chem.*, 276: 15728–15735, 2001), Favreau et al. (*Biochemistry*, 40: 14567–575, 2001), and/or U.S. Pat. No. 6,387,897 assigned to NeuroMed Technologies Inc.

Formulations

Formulations of the present invention may include, but are not limited to, continuous, as needed, short-term, rapid-offset, controlled release, sustained release, delayed release, and pulsatile release formulations.

One or more additional active agents can be administered with a Cav2.2 subunit calcium channel modulator either simultaneously or sequentially. The additional active agent will generally, although not necessarily, be one that is effective in treating a non-inflammatory GI tract disorder, and/or an agent that potentiates the effect of the Cav2.2 subunit calcium channel modulator. Suitable secondary agents include but are not limited to, for example, antiulceratives, antidiarrheals, peristaltic colon stimulants, antispasmodics, antinauseant/prokinetics, anti-inflammatory bowel drugs, tricyclic antidepressants, ketolarics, duloxetine, venlafaxine, monoamine reuptake inhibitors (including selective serotonin reuptake inhibitors (SSRI's) and serotonin/norepinephrine reuptake inhibitors (SNRI's)), spasmolytics, anticholinergics (particularly antimuscarinics), gabapentin, pregabalin, substituted aminomethyl-phenyl-cyclohexane derivatives including tramadol, 5-HT$_3$ antagonists, 5-HT$_4$ antagonists, β3 adrenergic agonists, neurokinin receptor antagonists, bradykinin receptor antagonists, nitric oxide donors and/or any agent that does not inhibit the action of the Cav2.2 subunit calcium channel modulator.

Antiulceratives that may be employed as additional active agents may include, for example, Aceglutamide Aluminum Complex, epsilon-Acetamidocaproic Acid Zinc Salt, Acetoxolone, Arbaprostil, Benexate Hydrochloride, Bismuth Subcitrate Sol (Dried), Carbenoxolone, Cetraxate, Cimetidine, Enprostil, Esaprazole, Famotidine, Ftaxilide, Gefarnate, Guaiazulene, Irsogladine, Misoprostil, Nizatidine, Omeprazole, Ornoprostil, .gamma.-Oryzanol, Pantoprazole, Pifarnine, Pirenzepine, Plaunotol,Rabeprazole, Ranitidine, Rioprostil, Rosaprostol, Rotraxate, Roxatidine Acetate, Sofaicone, Spizofurone, Sucralfate, Teprenone, Trimoprostil, Thrithiozine, Troxipide, Zolimidine.

Antidiarrheals that may be employed as additional active agents may include, for example, Acetyltannic Acid, Albumin Tannate, Alkofanone, alosetron, Aluminum Salicylates, Catechin, Cilansetron, Difenoxin, Diphenoxylate, Lidamidine, Loperamide, Mebiquine, Octreotide, Cholestyramine, Trillium, Uzarin, Aopectate, Pepto-Bismol, Lomotil, Codeine, Bisacodyl (Dulcolax), Cascara, Docusate (Colace), Pericolace (docusate/casanthranol), Psyllium (Metamucil), Dicyclomine (Bentyl), Propantheline (Pro-Banthine), Simethicone (Mylicon), and Donnatal.

Peristaltic colon stimulants that may be employed as additional active agents may include, for example, Tegaserod, Prucalopride, Lactulose, Magnesium hydroxide, and Miralax (PEG solutions).

Antispasmodic drugs that may be employed as additional active agents may include, for example, Alibendol, Ambucetamide, Aminopromazine, Apoatropine, Bevonium Methyl Sulfate, Bietamiverine, Butaverine, Butropium Bromide, N-Butylscopolammonium Bromide, Caroverine, Cimetropium Bromide, Cinnamedrine, Clebopride, Coniine Hydrobromide, Coniine Hydrochloride, Cyclonium Iodide, Difemerine, Diisopromine, Dioxaphetyl Butyrate, Diponium Bromide, Drofenine, Emepronium Bromide, Ethaverine, Feclemine, Fenalamide, Fenoverine, Fenpiprane, Fenpiverinium Bromide, Fentonium Bromide, Flavoxate, Flopropione, Gluconic Acid, Guaiactamine, Hydramitrazine, Hymecromone, Leiopyrrole, Mebeverine, Moxaverine, Nafiverine, Octamylamine, Octaverine, Pentapiperide, Phenamacide Hydrochloride, Phloroglucinol, Pinaverium Bromide, Piperilate, PipoxolanHydrochloride, Pramiverin, Prifinium Bromide, Properidine, Propivane, Propyromazine, Prozapine, Racefemine, Rociverine, Spasmolytol, Stilonium Iodide, Sultroponium, Tiemonium Iodide, Tiquizium Bromide, Tiropramide, Trepibutone, Tricromyl, Trifolium, Trimebutine, N,N-1Trimethyl-3,3-diphenyl-propylamine, Tropenzile, Trospium Chloride, and Xenytropium Bromide.

Antinauseant/prokinetic drugs that may be employed as additional active agents may include, for example, Acetylleucine Monoethanolamine, Alizapride, Benzquinamide, Bietanautine, Bromopride, Buclizine, Chlorpromazine, Cisparide, Clebopride, Cyclizine, Dimenhydrinate, Dipheniodol, Dolasetron, Domperidone, Droperidol, Granisetron, Meclizine, Methalltal, Metoclopramide, Metopimazine, Nabilone, Ondansteron, Oxypendyl, Pipamazine, Piprinhydrinate, Prochlorperazine, Scopolamine, Tetrahydrocannabinols, Thiethylperazine, Thioproperzaine and Trimethobenzamide.

Anti-inflammatory bowel drugs that may be employed as additional active agents may include, for example, Mesalamine, Sulfasalazine, Osalazine, Balsalazide, Corticosteroids, 6-Mercaptopurine, Azathioprine, Rapamycin, Methotrexate, Infliximab, Cyclosporine, Metronidazole, Ciprofloxacin, and Clarithromycin.

Any anticholinergic agent, specifically, any antimuscarinic agent, is useful as an additional active agent in the present invention. Compounds that have been identified as antimuscarinic agents and are useful as an additional active agent in the present invention include, but are not limited to:

a. Darifenacin (Daryon®);
b. YM-905 (solifenacin succinate);
c. Oxybutynin (Ditropan®);
d. S-Oxybutynin;
e. N-desethyl-oxybutynin;
f. Tolterodine (Detrol®);
g. Trospium (Uraplex®, Spasmex®);
h. Propiverine (Detrunorm®);
i. Propantheline bromide (Pro-Banthine®);
j. Hyoscyamine sulfate (Levsin®, Cystospaz®);
k. Dicyclomine hydrochloride (Bentyl®);
l. Flavoxate hydrochloride (Urispas®);
m. d,l (racemic) 4-diethylamino-2-butynyl phenylcyclohexylglycolate;
n. (R)-N,N-diisopropyl-3-(2-hydroxy-5-methylphenyl)-3-phenylpropanamine L-hydrogen tartrate;
o. (+)-(1S,3'R)-quinuclidin-3'-yl 1-phenyl-1,2,3,4-tetrahydroisoquinoline-2-carboxylate monosuccinate;
p. alpha(+)-4-(Dimethylamino)-3-methyl-1,2-diphenyl-2-butanol proprionate;
q. 1-methyl-4-piperidyl diphenylpropoxyacetate;
r. 3"-hydroxyspiro[1"H,5"H-nortropane-8,1'-pyrrolidinium benzilate;
s. 4 amino-piperidine containing compounds as disclosed in Diouf et al. (2002) *Bioorg. Med. Chem. Lett.* 12: 2535–9;
t. pirenzipine;
u. methoctramine;
v. 4-diphenylacetoxy-N-methyl piperidine methiodide;
w. tropicamide;
x. (2R)-N-[1-(6-aminopyridin-2-ylmethyl)piperidin-4-yl]-2-[(1R)-3,3-difluorocyclopentyl]-2-hydroxy-2-phenylacetamide; and
y. PNU-200577 ((R)-N,N-diisopropyl-3-(2-hydroxy-5-hydroxymethylphenyl)-3-phenylpropanamine).

The identification of further compounds that have antimuscarinic activity and would therefore be useful as an additional active agent in the present invention can be determined by performing muscarinic receptor binding specificity studies as described by Nilvebrant (2002) *Pharmacol. Toxicol.* 90: 260–7 or cystometry studies as described by Modiri et al (2002) *Urology* 59: 963–8.

Other agents useful in the present invention include any β3 adrenergic agonist agent. Compounds that have been identified as β3 adrenergic agonist agents and are useful in the present invention include, but are not limited to:

a. TT-138 and phenylethanolamine compounds as disclosed in U.S. Pat. No. 6,069,176, PCT Publication No. WO 97/15549 and available from Mitsubishi Pharma Corp.;
b. FR-149174 and propanolamine derivatives as disclosed in U.S. Pat. Nos. 6,495,546 and 6,391,915 and available from Fujisawa Pharmaceutical Co.;
c. KUC-7483, available from Kissei Pharmaceutical Co.,
d. 4'-hydroxynorephedrine derivatives such as 2-2-chloro-4-(2-((1S,2R)-2-hydroxy-2-(4-hydroxyphenyl)-1-methylethylamino)ethyl)phenoxy acetic acid as disclosed in Tanaka et al. (2003) *J. Med. Chem.* 46: 105–12;
e. 2-amino-1-phenylethanol compounds, such as BRL35135 ((R*R*)-(.+–.)-[4-[2-[2-(3-chlorophenyl)-2-ydroxyethylamino]propyl]phenox y]acetic acid methyl ester hydrobromide salt as disclosed in Japanese Patent Publication No. 26744 of 1988 and European Patent Publication No. 23385), and SR58611A ((RS)-N-(7-ethoxycarbonylmethoxy-1,2,3,4-tetrahydronaphth-2-yl)-2-(3-chlor ophenyl)-2-hydroxyethanamine hydrochloride as disclosed in Japanese Laid-open Patent Publication No. 66152 of 1989 and European Laid-open Patent Publication No. 255415);
f. GS 332 (Sodium (2R)-[3-[3-[2-(3 Chlorophenyl)-2-hydroxyethylamino]cyclohexyl]phenoxy]acetate) as disclosed in Iizuka et al. (1998) *J. Smooth Muscle Res.* 34: 139–49;
g. BRL-37,344 (4-[-[(2-hydroxy-(3-chlorophenyl)ethyl)-amino]propyl]phenoxyacetate) as disclosed in Tsujii et al. (1998) *Physiol. Behav.* 63: 723–8 and available from Glaxosmithkline;
h. BRL-26830A as disclosed in Takahashi et al. (1992) *Jpn Circ. J.* 56: 936–42 and available from Glaxosmithkline;
i. CGP 12177 (4-[3-t-butylamino-2-hydroxypropoxy]benzimidazol-2-one) (a β1/β2 adrenergic antagonist reported to act as an agonist for the β3 adrenergic receptor) as described in Tavernier et al. (1992) J. Pharmacol. Exp. Ther. 263: 1083–90 and available from Ciba-Geigy;
j. CL 316243 (R,R-5-[2-[[2-(3-chlorophenyl)-2-hydroxyethyl]amino]propyl]-1,3-benzodioxole-2,2-dicarboxylate) as disclosed in Berlan et al. (1994) *J. Pharmacol. Exp. Ther.* 268: 1444–51;
k. Compounds having β3 adrenergic agonist activity as disclosed in US Patent Application 20030018061;
l. ICI 215,001 HCl ((S)-4-[2-Hydroxy-3-phenoxypropylaminoethoxy]phenoxyacetic acid hydrochloride) as disclosed in Howe (1993) *Drugs Future* 18: 529 and available from AstraZeneca/ICI Labs;
m. ZD 7114 HCl (ICI D7114; (S)-4-[2-Hydroxy-3-phenoxypropylaminoethoxy]-N-(2-methoxyethyl)phenoxyacetamide HCl) as disclosed in Howe (1993) *Drugs Future* 18: 529 and available from AstraZeneca/ICI Labs;
n. Pindolol (1-(1H-lndol-4-yloxy)-3-[(1-methylethyl)amino]-2-propanol) as disclosed in Blin et al (1994) *Mol. Pharmacol.* 44: 1094;
o. (S)-(–)-Pindolol ((S)-1-(1H-indol-4-yloxy)-3-[(1-methylethyl)amino]-2-propanol) as disclosed in Walter et al (1984) *Naunyn-Schmied.Arch.Pharmacol.* 327: 159 and Kalkman (1989) *Eur.J.Pharmacol.* 173: 121;
p. SR 59230A HCl (1-(2-Ethylphenoxy)-3-[[(1S)-1,2,3,4-tetrahydro-1-naphthalenyl]amino]-(2S)-2-propanol hydrochloride) as disclosed in Manara et al. (1995) *Pharmacol. Comm.* 6: 253 and Manara et al. (1996) *Br. J. Pharmacol* 117: 435 and available from Sanofi-Midy;
q. SR 58611 (N[2s)7-carb-ethoxymethoxy-1,2,3,4-tetrahydronaphth]-(2r)-2-hydroxy-2(3-chlorophenyl) ethamine hydrochloride) as disclosed in Gauthier et al.

(1999) *J. Pharmacol. Exp. Ther*. 290: 687–693 and available from Sanofi Research;
r. Compound 427353 available from GlaxoSmithKline; and
s. L-796568 (N-[4-[2-[2(R)-Hydroxy-2-(3-pyridyl)ethylamino]ethyl]phenyl]-4-[4-[4-(trifluoromethyl)phenyl] thiazol-2-yl]benzenesulfonamide dihydrochloride) available from Merck & Co.

The identification of further compounds that have β3 adrenergic agonist activity and would therefore be useful in the present invention can be determined by performing radioligand binding assays and/or contractility studies as described by Zilberfarb et al. (1997) *J. Cell Sci*. 110: 801–807; Takeda et al. (1999) *J. Pharmacol. Exp. Ther*. 288: 1367–1373; and Gauthier et al. (1999) *J. Pharmacol. Exp. Ther*. 290: 687–693.

Any spasmolytic agent is also useful as an additional active agent in the present invention. Compounds that have been identified as spasmolytic agents and are useful as an additional active agent in the present invention include, but are not limited to:
a. α-α-diphenylacetic acid-4-(N-methyl-piperidyl) esters as disclosed in U.S. Pat. No. 5,897,875;
b. Human and porcine spasmolytic polypeptides in glycosylated form and variants thereof as disclosed in U.S. Pat. No. 5,783,416;
c. Dioxazocine derivatives as disclosed in U.S. Pat. No. 4,965,259;
d. Quaternary 6,11-dihydro-dibenzo-[b,e]-thiepine-11-N-alkylnorscopine ethers as disclosed in U.S. Pat. No. 4,608,377;
e. Quaternary salts of dibenzo[1,4]diazepinones, pyrido-[1,4]benzodiazepinones, pyrido[1,5]benzodiazepinones as disclosed in U.S. Pat. No. 4,594,190;
f. Endo-8,8-dialkyl-8-azoniabicyclo (3.2.1) octane-6,7-exo-epoxy-3-alkyl-carboxylate salts as disclosed in U.S. Pat. No. 4,558,054;
g. Pancreatic spasmolytic polypeptides as disclosed in U.S. Pat. No. 4,370,317;
h. Triazinones as disclosed in U.S. Pat. No. 4,203,983;
i. 2-(4-Biphenylyl)-N-(2-diethylamino alkyl)propionamide as disclosed in U.S. Pat. No. 4,185,124;
j. Piperazino-pyrimidines as disclosed in U.S. Pat. No. 4,166,852;
k. Aralkylamino carboxylic acids as disclosed in U.S. Pat. No. 4,163,060;
l. Aralkylamino sulfones as disclosed in U.S. Pat. No. 4,034,103;
m. Smooth muscle spasmolytic agents as disclosed in U.S. Pat. No. 6,207,852; and
n. papaverine.

The identification of further compounds that have spasmolytic activity and would therefore be useful as an additional active agent in the present invention can be determined by performing smooth muscle contractility studies as described in U.S. Pat. No. 6,207,852; Noronha-Blob et al. (1991) *J. Pharmacol. Exp. Ther*. 256: 562–567; and/or Kachur et al. (1988) *J. Pharmacol. Exp. Ther*. 247: 867–872.

Other agents useful in the present invention include any neurokinin receptor antagonist agent. Suitable neurokinin receptor antagonists for use in the present invention that act on the $NK_1$ receptor include, but are not limited to: 1-imino-2-(2-methoxy-phenyl)-ethyl)-7,7-diphenyl-4-perhydroisoindolone(3aR,7aR) ("RP 67580"); 2S,3S-cis-3-(2-methoxybenzylamino)-2-benzhydrylquinuclidine ("CP 96,345"); and (aR,9R)-7-[3,5-bis(trifluoromethyl)benzyl]-8,9,10,11-tetrahydro-9-methyl-5-(4-methylphenyl)-7H-[1,4] diazocino[2,1-g][1,7]naphthyridine-6,13-dione)("TAK-637"). Suitable neurokinin receptor antagonists for use in the present invention that act on the $NK_2$ receptor include but are not limited to: ((S)-N-methyl-N-4-(4-acetylamino-4-phenylpiperidino)-2-(3,4-dichloropheny l)butylbenzamide ("SR 48968"); Met-Asp-Trp-Phe-Dap-Leu ("MEN 10,627"); and cyc(Gln-Trp-Phe-Gly-Leu-Met) ("L 659,877"). The identification of further compounds that have neurokinin receptor antagonist activity and would therefore be useful in the present invention can be determined by performing binding assay studies as described in Hopkins et al. (1991) *Biochem. Biophys. Res. Comm*. 180: 1110–1117; and Aharony et al. (1994) Mol. Pharmacol. 45: 9–19.

Other agents useful in the present invention include any bradykinin receptor antagonist agent. Suitable bradykinin receptor antagonists for use in the present invention that act on the $B_1$ receptor include but are not limited to: des-arg$^{10}$HOE 140 (available from Hoechst Pharmaceuticals) and des-Arg$^9$bradykinin (DABK). Suitable bradykinin receptor antagonists for use in the present invention that act on the $B_2$ receptor include but are not limited to: D-Phe$^7$-BK; D-Arg-(Hyp$^3$-Thi$^{5,8}$-D-Phe$^7$)-BK ("NPC 349"); D-Arg-(Hyp$^3$-D-Phe$^7$)-BK ("NPC 567"); D-Arg-(Hyp$^3$-Thi$^5$-D-Tic$^7$-Oic$^8$)-BK ("HOE 140"); H-DArg-Arg-Pro-Hyp-Gly-Thi-c(Dab-DTic-Oic-Arg)c(7gamma-10alpha) ("MEN11270"); H-DArg-Arg-Pro-Hyp-Gly-Thi-Ser-DTic-Oic-Arg-OH("Icatibant"); (E)-3-(6-acetamido-3-pyridyl)-N-[N-[2, 4-dichloro-3-[(2-methyl-8-quinolinyl) oxymethyl] phenyl]-N-methylaminocarbonylmethyl]acrylamide ("FR173567"); and WIN 64338.

These compounds are more fully described in Perkins, M. N., et. al., *Pain*, supra; Dray, A., et. al., *Trends Neurosci*., supra; and Meini et al. (2000) *Eur. J Pharmacol*. 388: 177–82. The identification of further compounds that have bradykinin receptor antagonist activity and would therefore be useful in the present invention can be determined by performing binding assay studies as described in Manning et al. (1986) *J. Pharmacol. Exp. Ther*. 237: 504 and U.S. Pat. No. 5,686,565.

Other agents useful in the present invention include any nitric oxide donor agent. Suitable nitric oxide donors for the practice of the present invention include but are not limited to:
a. Nitroglycerin;
b. Sodium nitroprusside;
c. FK 409 (NOR-3);
d. FR 144420 (NOR-4);
e. 3-morpholinosydnonimine;
f. Linsidomine chlorohydrate ("SIN-1");
g. S-nitroso-N-acetylpenicillamine ("SNAP");
h. AZD3582 (CINOD lead compound, available from NicOx S.A.);
i. NCX 4016 (available from NicOx S.A.);
j. NCX 701 (available from NicOx S.A.);
k. NCX 1022 (available from NicOx S.A.);
l. HCT 1026 (available from NicOx S.A.);
m. NCX 1015 (available from NicOx S.A.);
n. NCX 950 (available from NicOx S.A.);
o. NCX 1000 (available from NicOx S.A.);
p. NCX 1020 (available from NicOx S.A.);
q. AZD 4717 (available from NicOx S.A.);
r. NCX 1510/NCX 1512 (available from NicOx S.A.);
S. NCX 2216 (available from NicOx S.A.);
t. NCX 4040 (available from NicOx S.A.);

U. Nitric oxide donors as disclosed in U.S. Pat. No. 5,155,137;

v. Nitric oxide donors as disclosed in U.S. Pat. No. 5,366,997;

w. Nitric oxide donors as disclosed in U.S. Pat. No. 5,405,919;

x. Nitric oxide donors as disclosed in U.S. Pat. No. 5,650,442;

y. Nitric oxide donors as disclosed in U.S. Pat. No. 5,700,830;

z. Nitric oxide donors as disclosed in U.S. Pat. No. 5,632,981;

aa. Nitric oxide donors as disclosed in U.S. Pat. No. 6,290,981;

bb. Nitric oxide donors as disclosed in U.S. Pat. No. 5,691,423;

cc. Nitric oxide donors as disclosed in U.S. Pat. No. 5,721,365;

dd. Nitric oxide donors as disclosed in U.S. Pat. No. 5,714,511;

ee. Nitric oxide donors as disclosed in U.S. Pat. No. 6,511,911; and ff. Nitric oxide donors as disclosed in U.S. Pat. No. 5,814,666.

The identification of further compounds that have nitric oxide donor activity and would therefore be useful in the present invention can be determined by release profile and/or induced vasospasm studies as described in U.S. Pat. Nos. 6,451,337 and 6,358,536, as well as Moon (2002) *IBJU Int.* 89: 942–9 and Fathian-Sabet et al. (2001) *J Urol.* 165: 1724–9.

Gabapentin (Neurontin, or 1-(aminomethyl) cyclohexaneacetic acid) is an anticonvulsant drug with a high binding affinity for some calcium channel subunits. Although gabapentin was originally developed as a GABA-mimetic compound to treat spasticity, gabapentin has no direct GABAergic action and does not block GABA uptake or metabolism. (For review, see Rose et al. (2002) *Analgesia* 57:451–462). Gabapentin has been found, however, to be an effective treatment for the prevention of partial seizures in patients who are refractory to other anticonvulsant agents (Chadwick (1991) *Gabapentin*, In Pedley T A, Meldrum B S (eds.), *Recent Advances in Epilepsy*, Churchill Livingstone, New York, pp. 211–222).

In addition to its known anticonvulsant effects, gabapentin has been shown to block the tonic phase of nociception induced by formalin and carrageenan, and exerts an inhibitory effect in neuropathic pain models of mechanical hyperalgesia and mechanical/thermal allodynia (Rose et al. (2002) *Analgesia* 57: 451–462). Double-blind, placebo-controlled trials have indicated that gabapentin is an effective treatment for painful symptoms associated with diabetic peripheral neuropathy, post-herpetic neuralgia, and neuropathic pain (see, e.g., Backonja et al. (1998) *JAMA* 280: 1831–1836; Mellegers et al. (2001) *Clin. J. Pain* 17:284–95).

Pregabalin, (S)-(3-aminomethyl)-5-methylhexanoic acid or (S)-isobutyl GABA, is another GABA analog whose use as an anticonvulsant has been explored (Bryans et al. (1998) *J. Med. Chem.* 41:1838–1845).

The substituted aminomethyl-phenyl-cyclohexane derivatives suitable for use in the invention are represented by structural Formula I:

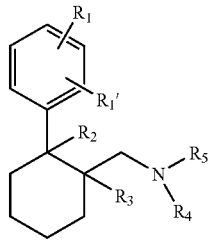

and enantiomers and mixtures thereof wherein:

$R_1$ and $R_1'$ are independently hydrogen, an aliphatic group, an aryl group, an arylalkyl group, a halogen, —CN, —$OR_6$, —$SR_6$, —$NR_6R_6$, —$OC(O)R_6$, —$C(O)OR_6$, —$C(O)R_6$ or —$C(O)NR_6R_6$;

$R_2$ is hydrogen, halogen, —$OR_7$ or —$OC(O)R_7$;

$R_3$ is hydrogen or an aliphatic group;

or $R_2$ and $R_3$ together form a double bond;

$R_4$ and $R_5$ are independently hydrogen, an aliphatic group, an aryl group, or an arylalkyl group;

$R_6$ is hydrogen, an aliphatic group, an aryl group or an arylalkyl group;

$R_7$ is hydrogen, an aliphatic group, an aryl group or an arylalkyl group;

or pharmaceutically acceptable salts, solvates or hydrates thereof.

In a particular embodiment of Formula I, $R_2$ is —OH. When $R_2$ is —OH, it is preferred that $R_1'$ is hydrogen and $R_1$ is $OCH_3$, preferably substituted at the meta position of the phenyl ring.

In a further embodiment of Formula I, $R_2$ is —OH, $R_1'$ is hydrogen and $R_1$ is —$OR_6$, substituted at the meta position of the phenyl ring and $R_6$ is an aliphatic group, for example, and alkyl group. In a particular embodiment, wherein $R_2$ is —OH, $R_1'$ is hydrogen and $R_1$ is —$OR_6$, substituted at the meta position of the phenyl ring and $R_6$ is an alkyl group, $R_3$, $R_4$ and $R_5$ can be hydrogen or an alkyl group.

In one embodiment, the substituted aminomethyl-phenyl-cyclohexane derivative suitable for use in the invention is represented by structural Formula II:

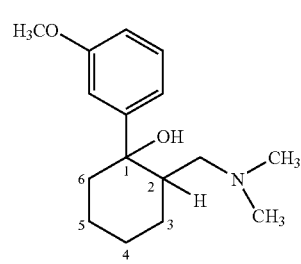

and enantiomers and mixtures thereof or pharmaceutically acceptable salts, solvates or hydrates thereof.

In a particular embodiment, the compound of Formula II is a mixture of the (+)cis and (−)cis enantiomers, wherein the C-1 and C-2 carbons of the cyclohexyl ring are (1R,2R) and (1S,2S), respectively, and the substituents on C-1 and C-2 are in the cis orientation.

In a specific embodiment, the mixture of the (+)cis and (−)cis enantiomers is a racemic mixture. That is, the compound of Formula II is a 50:50 mixture of (+)cis and (−)cis enantiomers as shown below:

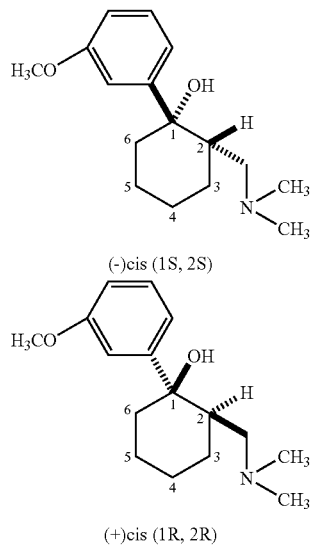

(−)cis (1S, 2S)

(+)cis (1R, 2R)

In other words, the compound of Formula II is the 50:50 mixture of (+/−)cis-2-[(dimethylamino)methyl]-1-(3-methoxyphenyl) cyclohexanol, commonly referred to as tramadol. The compound can be in the form of a pharmaceutically acceptable salt. Typically, tramadol is administered in the form of the hydrochloride salt. The tramadol hydrochloride is also known, for example, by the tradename ULTRAM®.

Tramadol in the form of the hydrochloride salt, is widely used as an analgesic. Tramadol is a centrally acting analgesic with a low affinity for opioid receptors. In contrast to other opioids, the analgesic action of tramadol is only partially inhibited by the opioid antagonist naloxone, which suggests the existence of an additional non-opioid mechanism of action. It has been found that monoaminergic activity, wherein noradrenaline and serotonin (5-HT) reuptake are inhibited, contributes significantly to the analgesic action of tramadol by blocking nociceptive impulses at the spinal level.

In a further embodiment, the administered compound is the (+)cis enantiomer of tramadol, set forth above.

In another embodiment, the substituted aminomethyl-phenyl-cyclohexane derivative is represented by the following structural Formula III in which the nitrogen of the aminomethyl group is in the form of the N-oxide:

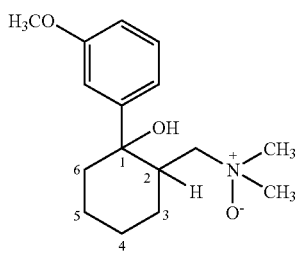

III and enantiomers and mixtures thereof or pharmaceutically acceptable salts, solvates and hydrates thereof.

In a particular embodiment, the compound of Formula III is a mixture of the (+)cis and (−)cis enantiomers, wherein the C-1 and C-2 carbons of the cyclohexyl ring are (1R,2R) and (1S,2S), respectively, and the substituents on C-1 and C-2 are in the cis orientation.

In a specific embodiment, the mixture of the (+)cis and (−)cis enantiomers is a racemic mixture. That is, the compound of Formula III is a 50:50 mixture of (+)cis and (−)cis enantiomers as shown below:

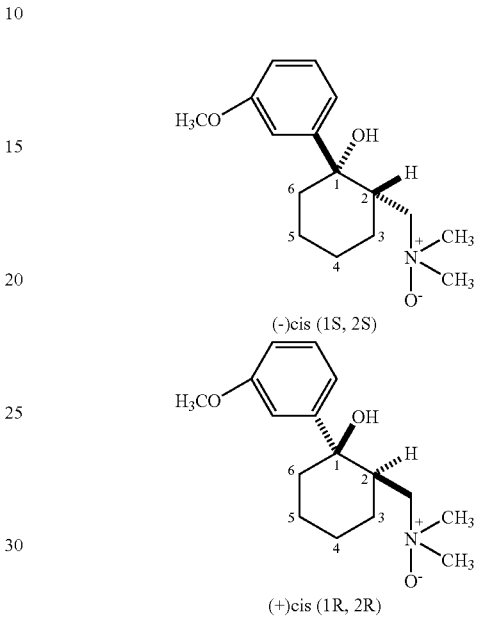

(−)cis (1S, 2S)

(+)cis (1R, 2R)

In other words, the compound of Formula III is the 50:50 mixture of the N-oxide of (+/−)cis-2-[(dimethylamino)methyl]-1-(3-methoxyphenyl) cyclohexanol.

In a further embodiment, the N-oxide is predominantly the (+)cis enantiomer, as set forth above.

In one embodiment, the substituted aminomethyl-phenyl-cyclohexane derivative suitable for use in the invention is represented by structural Formula IV:

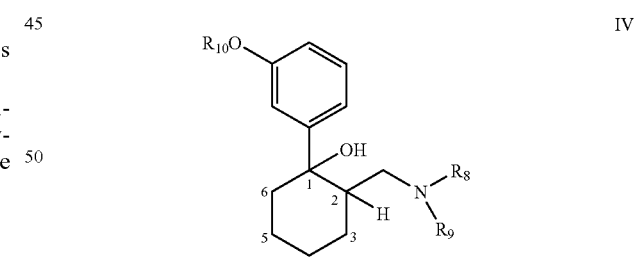

IV and enantiomers and mixtures thereof wherein:
$R_8$, $R_9$ and $R_{10}$ are independently hydrogen or an alkyl group;
or pharmaceutically acceptable salts, solvates or hydrates thereof.

In a particular embodiment, the compound of Formula IV is a mixture of the (+)cis and (−)cis enantiomers, wherein the C-1 and C-2 carbons of the cyclohexyl ring are (1R,2R) and (1S,2S), respectively, and the substituents on C-1 and C-2 are in the cis orientation.

In a specific embodiment, the mixture of the (+)cis and (−)cis enantiomers is a racemic mixture. That is, the compound of Formula IV is a 50:50 mixture of (+)cis and (−)cis enantiomers as shown below:

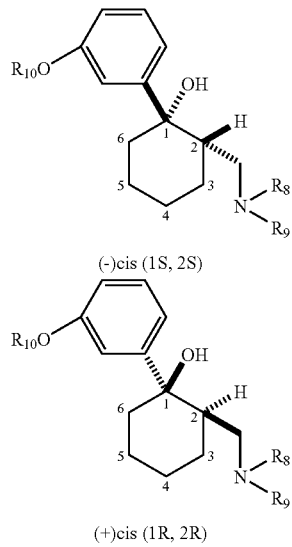

In a further embodiment, the compounds of Formula IV are predominantly the (+)cis enantiomer, as set forth above.

In a particular embodiment $R_{10}$ is hydrogen. In a further embodiment wherein $R_{10}$ is hydrogen, $R_8$ and $R_9$ are independently hydrogen or an alkyl group, for example, a methyl group. When $R_{10}$ is hydrogen and $R_8$ and $R_9$ are methyl groups, and Formula IV is the racemic mixture of the (+)cis and (−)cis enantiomers, the compound can be referred to as O-desmethyltramadol. The specific (+) and (−) enantiomers set forth above, can be referred to as (+)O-desmethyltramadol and (−)O-desmethyltramadol.

In yet another embodiment, R10 is hydrogen, R8 is hydrogen and $R_9$ is a methyl group. When $R_{10}$ is hydrogen, $R_8$, is hydrogen and $R_9$ is a methyl group, and Formula IV is the racemic mixture of the (+)cis and (−)cis enantiomers, the compound can be referred to as O-desmethyl-N-mono-desmethyl-tramadol. The specific (+)cis and (−)cis enantiomers as set forth above can be referred to as (+)O-desmethyl-N-mono-desmethyl-tramadol and (−)O-desmethyl-N-mono-desmethyl-tramadol.

In yet another embodiment, the substituted aminomethyl-phenyl-cyclohexane derivative is represented by structural Formula V:

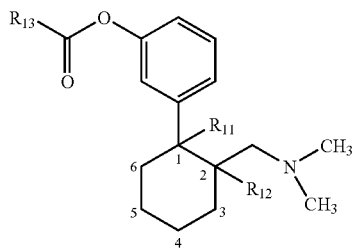

and enantiomers and mixtures thereof wherein:
$R_{11}$ is —OH;
$R_{12}$ is hydrogen or $R_{11}$ and $R_{12}$ together form a double bond;
$R_{13}$ is an aryl group selected from the group consisting of:

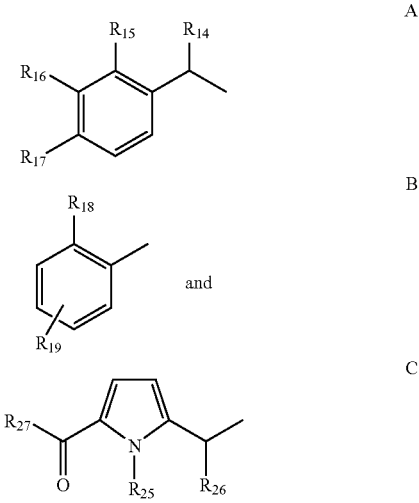

wherein:
$R_{14}$ is hydrogen or an alkyl group;
$R_{15}$ is hydrogen, —NH$_2$, —NHR$_{20}$ or —OR$_{20}$;
$R_{16}$ is hydrogen, —COR$_{20}$, —OR$_{20}$ or halogen;
$R_{17}$ is hydrogen, an alkyl group, —O-alkenyl, a phenyl group or $R_{16}$ and $R_{17}$ are —CH=CR$_{21}$–CR$_{22}$+CH—, forming an aromatic ring;
$R_{18}$ is hydrogen, —COR$_{23}$, —OR$_{24}$ or a halogen;
$R_{19}$ is hydrogen, halogen, an alkyl group, —O-alkyl, —NO$_2$ or an aryl group;
$R_{20}$ is a phenyl group optionally substituted by one or more of the following: halogen, —NO$_2$, an alkyl group, an alkenyl group, —OH or —NH$_2$;
$R_{21}$ and $R_{22}$ are independently hydrogen or —O-alkyl;
$R_{23}$ is a phenyl group optionally substituted by one or more of the following: halogen, —NO2, an alkyl group, and alkenyl group, —OH or —NH$_2$;
$R_{24}$ is hydrogen, —CO-alkyl (preferably methyl) or a phenyl group optionally substituted by one or more of the following: halogen, —NO$_2$, an alkyl group, and alkenyl group, —OH or —NH$_2$;
$R_{25}$ and $R_{26}$ are independently hydrogen, an alkyl group or form a —CH$_2$—$_{CH2}$— group;
$R_{27}$ is a phenyl group optionally substituted by one or more of the following: halogen, —NO$_2$, an alkyl group, an alkenyl group, —OH or —NH$_2$;
or pharmaceutically acceptable salts, solvates or hydrates thereof.

In a particular embodiment of Formula V, $R_{11}$ is —OH, $R_{12}$ is H and $R_{13}$ is:

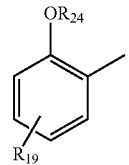

wherein:

$R_{24}$ is hydrogen or —COCH$_3$;

$R_{19}$ is halogen, an alkyl group, —O-alkyl or —NO$_2$.

It is preferred that when $R_{19}$ is —O-alkyl, the alkyl group is a methyl group.

It is preferred that when $R_{19}$ is an alkyl group, the alkyl group is substituted with one or more halogens. For example the substituted alkyl group is —CF$_3$.

Substituted aminomethyl-phenyl-cyclohexane derivatives in accordance with Formula V are further described in U.S. Pat. No. 6,455,585 and published PCT Application WO01/49650, which are incorporated herein by reference.

5-HT$_3$ antagonists that may be employed as additional active agents in the present invention include, but are not limited to:

a. Ondansetron [1,2,3,9-tetrahydro-9-methyl-3-[(2-methyl-1H-imidazol-1-yl]methyl]-4H-carb azol-4-one (cf. Merck Index, twelfth edition, item 6979);

b. Granisetron [endo-1-methyl-N-(9-methyl-9-aza-bicyclo[3.3.1]non-3-yl)-1H-imidazole-3-carboxamide: (cf. Merck Index, twelfth edition, item 4557);

c. Dolasetron [1H-indole-3-carboxylic acid (2. alpha., 6. alpha., 8. alpha., 9. alpha. .beta.)-octahydro-3-oxo-2, 6methano-2H-quinolizin-8-yl ester] (cf. Merck Index, twelfth edition, item 3471);

d. Indol-3-yl-carboxylic acid-endo-8-methyl-8-aza-bicyclo[3,2,1]-oct-3-yl-ester, also known as tropisetron. (cf. Merck Index, twelfth edition, item 9914);

e. 4,5,6,7-tetrahydro-5-[(1-methyl-indol-3yl)carbonyl] benzimidazole (see also ramosetron, U.S. Pat. No. 5,344,927);

f. (+)-10-methyl-7-(5-methyl-1H-imidazol-4-ylmethyl)-6,7,8,9-tetrahydropyrido [1,2-a]indol-6-one (see also fabesetron, European Patent No. 0 361 317);

g. [N-(1-ethyl-2-imidazolin-2-yl-methyl)-2-methoxy-4-amino-5-chlorobenzamide (see also lintopride-Chem.-Abstr.-No. 107429-63-0); and h. 2,3,4,5-tetrahydro-5-methyl-2-[(5-methyl-1H-imidazol-4-yl)methyl]-1H-pyrid o[4,3-b]indol-1-one (see also alosetron, European Patent No. 0 306 323).

5-HT$_4$ antagonists that may be employed as additional active agents in the present invention include, but are not limited to benzopyran, benzothiopyran and benzofuran derivatives as disclosed in U.S. Pat. No. 6,127,379.

Other agents useful in the present invention include any neurokinin receptor antagonist agent. Suitable neurokinin receptor antagonists for use in the present invention that act on the NK$_1$ receptor include, but are not limited to: 1-imino-2-(2-methoxy-phenyl)-ethyl)-7,7-diphenyl-4-perhydroisoindolone(3aR ,7aR) ("RP 67580"); 2S,3S-cis-3-(2-methoxybenzylamino)-2-benzhydrylquinuclidine ("CP 96,345"); and (aR,9R)-7-[3,5-bis(trifluoromethyl)benzyl]-8,9,10,11-tetrahydro-9-methyl-5-(4-methylphenyl)-7H-[1,4] diazocino[2,1-g][1,7]naphthyridine-6,13-dione)("TAK-637"). Suitable neurokinin receptor antagonists for use in the present invention that act on the NK$_2$ receptor include but are not limited to: ((S)-N-methyl-N-4-(4-acetylamino-4-phenylpiperidino)-2-(3,4-dichlorophenyl)butylbenzamide ("SR 48968"); Met-Asp-Trp-Phe-Dap-Leu ("MEN 10,627"); and cyc(Gln-Trp-Phe-Gly-Leu-Met) ("L 659,877"). The identification of further compounds that have neurokinin receptor antagonist activity and would therefore be useful in the present invention can be determined by performing binding assay studies as described in Hopkins et al. (1991) *Biochem. Biophys. Res. Comm.* 180: 1110–1117; and Aharony et al. (1994) Mol. Pharmacol. 45: 9–19.

Other agents useful in the present invention include any bradykinin receptor antagonist agent. Suitable bradykinin receptor antagonists for use in the present invention that act on the B$_1$ receptor include but are not limited to: des-arg$^{10}$HOE 140 (available from Hoechst Pharmaceuticals) and des-Arg$^9$bradykinin (DABK). Suitable bradykinin receptor antagonists for use in the present invention that act on the B$_2$ receptor include but are not limited to: D-Phe$^7$-BK; D-Arg-(Hyp$^3$-Thi$^{5,8}$-D-Phe$^7$)-BK ("NPC 349"); D-Arg-(Hyp$^3$-D-Phe$^7$)-BK ("NPC 567"); D-Arg-(Hyp$^3$-Thi$^5$-D-Tic$^7$-Oic$^8$)-BK ("HOE 140"); H-DArg-Arg-Pro-Hyp-Gly-Thi-c(Dab-DTic-Oic-Arg)c(7gamma-10alpha) ("MEN11270"); H-DArg-Arg-Pro-Hyp-Gly-Thi-Ser-DTic-Oic-Arg-OH("Icatibant"); (E)-3-(6-acetamido-3-pyridyl)-N-[N-[2,4-dichloro-3-[(2-methyl-8-quinolinyl) oxymethyl] phenyl]-N-methylaminocarbonylmethyl]acrylamide ("FR173567"); and WIN 64338. These compounds are more fully described in Perkins, M. N., et. al., *Pain*, supra; Dray, A., et. al., *Trends Neurosci.*, supra; and Meini et al. (2000) *Eur. J. Pharmacol.* 388: 177–82. The identification of further compounds that have bradykinin receptor antagonist activity and would therefore be useful in the present invention can be determined by performing binding assay studies as described in Manning et al. (1986) *J. Pharmacol. Exp. Ther.* 237: 504 and U.S. Pat. No. 5,686,565.

Any of the active agents may be administered in the form of a salt, ester, amide, prodrug, active metabolite, derivative, enantiomer, diastereomer, or the like, provided that the salt, ester, amide, prodrug or derivative is suitable pharmacologically, i.e., effective in the present method. Salts, esters, amides, prodrugs, enantiomers, diastereomers, and other derivatives of the active agents may be prepared using standard procedures known to those skilled in the art of synthetic organic chemistry and described, for example, by J. March, Advanced Organic Chemistry: Reactions, Mechanisms and Structure, 4$^{th}$ Ed. (New York: Wiley-Interscience, 1992). For example, acid addition salts are prepared from the free base using conventional methodology, and involves reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are salts prepared with organic acids. Conversely, preparation of basic salts of acid moieties which may be present on an active agent are prepared in a similar manner using a pharmaceutically acceptable base such as sodium hydroxide, potassium hydroxide, ammonium hydroxide, calcium hydroxide, trimethylamine, or the like. Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety, which results in a compound that is therapeutically inactive until modified by an individual's metabolic system.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Pharmaceutical Compositions and Dosage Forms

Suitable compositions and dosage forms include tablets, capsules, caplets, pills, gel caps, troches, dispersions, suspensions, solutions, syrups, transdermal patches, gels, powders, magmas, lozenges, creams, pastes, plasters, lotions, discs, suppositories, liquid sprays for nasal or oral administration, dry powder or aerosolized formulations for inhalation, ointments, liquid formulations, pessaries, tampons, foams and the like. Further, those of ordinary skill in the art can readily deduce that suitable formulations involving these compositions and dosage forms, including those formulations as described elsewhere herein.

Oral Dosage Forms

Oral dosage forms include tablets, capsules, caplets, solutions, suspensions and/or syrups, and may also comprise a plurality of granules, beads, powders or pellets that may or may not be encapsulated. Such dosage forms are prepared using conventional methods known to those in the field of pharmaceutical formulation and described in the pertinent texts, e.g., in Remington: The Science and Practice of Pharmacy, supra. Tablets and capsules represent the most convenient oral dosage forms, in which case solid pharmaceutical carriers are employed.

Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In addition to the active agent(s), then, tablets prepared for oral administration using the method of the invention will generally contain other materials such as binders, diluents, lubricants, disintegrants, fillers, stabilizers, surfactants, preservatives, coloring agents, flavoring agents and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

The dosage form may also be a capsule, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. (See, for e.g., Remington: The Science and Practice of Pharmacy, supra), which describes materials and methods for preparing encapsulated pharmaceuticals. If the active agent-containing composition is present within the capsule in liquid form, a liquid carrier is necessary to dissolve the active agent(s). The carrier must be compatible with the capsule material and all components of the pharmaceutical composition, and must be suitable for ingestion.

Solid dosage forms, whether tablets, capsules, caplets, or particulates, may, if desired, be coated so as to provide for delayed release. Dosage forms with delayed release coatings may be manufactured using standard coating procedures and equipment. Such procedures are known to those skilled in the art and described in the pertinent texts (See, for e.g., Remington: The Science and Practice of Pharmacy, supra). Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Sustained release dosage forms provide for drug release over an extended time period, and may or may not be delayed release. Generally, as will be appreciated by those of ordinary skill in the art, sustained release dosage forms are formulated by dispersing a drug within a matrix of a gradually bioerodible (hydrolyzable) material such as an insoluble plastic, a hydrophilic polymer, or a fatty compound, or by coating a solid, drug-containing dosage form with such a material. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

Transmucosal Compositions and Dosage Forms

Although the present compositions may be administered orally, other modes of administration are suitable as well. For example, transmucosal administration may be advantageously employed. Transmucosal administration is carried out using any type of formulation or dosage unit suitable for application to mucosal tissue. For example, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, administered by inhalation of an aerosol formulation, a non-aerosol liquid formulation, or a dry powder, placed within or near the rectum ("transrectal" formulations), or administered to the urethra as a suppository, ointment, or the like.

Preferred buccal dosage forms will typically comprise a therapeutically effective amount of an active agent and a bioerodible (hydrolyzable) polymeric carrier that may also serve to adhere the dosage form to the buccal mucosa. The buccal dosage unit is fabricated so as to erode over a predetermined time period, wherein drug delivery is provided essentially throughout. The time period is typically in the range of from about 1 hour to about 72 hours. Preferred buccal delivery preferably occurs over a time period of from about 2 hours to about 24 hours. Buccal drug delivery for short term use should preferably occur over a time period of from about 2 hours to about 8 hours, more preferably over a time period of from about 3 hours to about 4 hours. As needed buccal drug delivery preferably will occur over a time period of from about 1 hour to about 12 hours, more preferably from about 2 hours to about 8 hours, most preferably from about 3 hours to about 6 hours. Sustained buccal drug delivery will preferably occur over a time period of from about 6 hours to about 72 hours, more preferably from about 12 hours to about 48 hours, most preferably from about 24 hours to about 48 hours. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver.

The "therapeutically effective amount" of the active agent in the buccal dosage unit will of course depend on the potency of the agent and the intended dosage, which, in turn, is dependent on the particular individual undergoing treatment, the specific indication, and the like. The buccal dosage unit will generally contain from about 1.0 wt. % to about 60 wt. % active agent, preferably on the order of from about 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with the Cav2.2 subunit calcium channel modulator to be administered and any other components of the buccal dosage unit. Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (Carbopol®, which may be obtained from B. F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Sublingual and lingual dosage forms include tablets, creams, ointments, lozenges, pastes, and any other solid dosage form where the active ingredient is admixed into a disintegrable matrix. The tablet, cream, ointment or paste for sublingual or lingual delivery comprises a therapeutically effective amount of the selected active agent and one or more conventional nontoxic carriers suitable for sublingual or lingual drug administration. The sublingual and lingual dosage forms of the present invention can be manufactured using conventional processes. The sublingual and lingual dosage units are fabricated to disintegrate rapidly. The time period for complete disintegration of the dosage unit is typically in the range of from about 10 seconds to about 30 minutes, and optimally is less than 5 minutes.

Other components may also be incorporated into the sublingual and lingual dosage forms described herein. The additional components include, but are not limited to binders, disintegrants, wetting agents, lubricants, and the like. Examples of binders that may be used include water, ethanol, polyvinylpyrrolidone; starch solution gelatin solution, and the like. Suitable disintegrants include dry starch, calcium carbonate, polyoxyethylene sorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual and lingual dosage forms are known, or will be apparent, to those skilled in this art (See, e.g., Remington: The Science and Practice of Pharmacy, supra).

For transurethral administration, the formulation comprises a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

Depending on the particular active agent administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("$C_{10}$ MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Mass.), surfactants as discussed above, including, for example, Tergitol®, Nonoxynol-9® and TWEEN-80®, and lower alkanols such as ethanol.

Transurethral drug administration, as explained in U.S. Pat. Nos. 5,242,391, 5,474,535, 5,686,093 and U.S. Pat. No. 5,773,020, can be carried out in a number of different ways using a variety of urethral dosage forms. For example, the drug can be introduced into the urethra from a flexible tube, squeeze bottle, pump or aerosol spray. The drug may also be contained in coatings, pellets or suppositories that are absorbed, melted or bioeroded in the urethra. In certain embodiments, the drug is included in a coating on the exterior surface of a penile insert. It is preferred, although not essential, that the drug be delivered from at least about 3 cm into the urethra, and preferably from at least about 7 cm into the urethra. Generally, delivery from at least about 3 cm to about 8 cm into the urethra will provide effective results in conjunction with the present method.

Urethral suppository formulations containing PEG or a PEG derivative may be conveniently formulated using conventional techniques, e.g., compression molding, heat molding or the like, as will be appreciated by those skilled in the art and as described in the pertinent literature and pharmaceutical texts. (See, e.g., Remington: The Science and Practice of Pharmacy, supra), which discloses typical methods of preparing pharmaceutical compositions in the form of urethral suppositories. The PEG or PEG derivative preferably has a molecular weight in the range of from about 200 to about 2,500 g/mol, more preferably in the range of from about 1,000 to about 2,000 g/mol. Suitable polyethylene glycol derivatives include polyethylene glycol fatty acid esters, for example, polyethylene glycol monostearate, polyethylene glycol sorbitan esters, e.g., polysorbates, and the like. Depending on the particular active agent, it may also be preferred that urethral suppositories contain one or more solubilizing agents effective to increase the solubility of the active agent in the PEG or other transurethral vehicle.

It may be desirable to deliver the active agent in a urethral dosage form that provides for controlled or sustained release of the agent. In such a case, the dosage form comprises a biocompatible, biodegradable material, typically a biodegradable polymer. Examples of such polymers include polyesters, polyalkylcyanoacrylates, polyorthoesters, polyanhydrides, albumin, gelatin and starch. As explained, for example, in PCT Publication No. WO 96/40054, these and other polymers can be used to provide biodegradable microparticles that enable controlled and sustained drug release, in turn minimizing the required dosing frequency.

The urethral dosage form will preferably comprise a suppository that is on the order of from about 2 to about 20 mm in length, preferably from about 5 to about 10 mm in length, and less than about 5 mm in width, preferably less than about 2 mm in width. The weight of the suppository will typically be in the range of from about 1 mg to about 100 mg, preferably in the range of from about 1 mg to about 50 mg. However, it will be appreciated by those skilled in the art that the size of the suppository can and will vary, depending on the potency of the drug, the nature of the formulation, and other factors.

Transurethral drug delivery may involve an "active" delivery mechanism such as iontophoresis, electroporation or phonophoresis. Devices and methods for delivering drugs in this way are well known in the art. Iontophoretically assisted drug delivery is, for example, described in PCT Publication No. WO 96/40054, cited above. Briefly, the active agent is driven through the urethral wall by means of an electric current passed from an external electrode to a second electrode contained within or affixed to a urethral probe.

Preferred transrectal dosage forms include rectal suppositories, creams, ointments, and liquid formulations (enemas). The suppository, cream, ointment or liquid formulation for transrectal delivery comprises a therapeutically effective amount of the selected active agent and one or more conventional nontoxic carriers suitable for transrectal drug administration. The transrectal dosage forms of the present invention can be manufactured using conventional processes. The transrectal dosage unit can be fabricated to disintegrate rapidly or over a period of several hours. The time period for complete disintegration is preferably in the range of from about 10 minutes to about 6 hours, and optimally is less than about 3 hours.

Other components may also be incorporated into the transrectal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

Preferred vaginal or perivaginal dosage forms include vaginal suppositories, creams, ointments, liquid formulations, pessaries, tampons, gels, pastes, foams or sprays. The suppository, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention can be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and U.S. Pat. No. 6,086,909). The vaginal or perivaginal dosage unit can be fabricated to disintegrate rapidly or over a period of several hours. The time period for complete disintegration is preferably in the range of from about 10 minutes to about 6 hours, and optimally is less than about 3 hours.

Other components may also be incorporated into the vaginal or perivaginal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

The active agents may also be administered intranasally or by inhalation. Compositions for intranasal administration are generally liquid formulations for administration as a spray or in the form of drops, although powder formulations for intranasal administration, e.g., insufflations, are also known, as are nasal gels, creams, pastes or ointments. For liquid formulations, the active agent can be formulated into a solution, e.g., water or isotonic saline, buffered or unbuffered, or as a suspension. Preferably, such solutions or suspensions are isotonic relative to nasal secretions and of about the same pH, ranging e.g., from about pH 4.0 to about pH 7.4 or, from about pH 6.0 to about pH 7.0. Buffers should be physiologically compatible and include, simply by way of example, phosphate buffers. Furthermore, various devices are available in the art for the generation of drops, droplets and sprays, including droppers, squeeze bottles, and manually and electrically powered intranasal pump dispensers. Active agent containing intranasal carriers may also include nasal gels, creams, pastes or ointments with a viscosity of, e.g., from about 10 to about 6500 cps, or greater, depending on the desired sustained contact with the nasal mucosal surfaces. Such carrier viscous formulations may be based upon, simply by way of example, alkylcelluloses and/or other biocompatible carriers of high viscosity well known to the art (see e.g., Remington: The Science and Practice of Pharmacy, supra). Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. Formulations for inhalation may be prepared as an aerosol, either a solution aerosol in which the active agent is solubilized in a carrier (e.g., propellant) or a dispersion aerosol in which the active agent is suspended or dispersed throughout a carrier and an optional solvent. Non-aerosol formulations for inhalation may take the form of a liquid, typically an aqueous suspension, although aqueous solutions may be used as well. In such a case, the carrier is typically a sodium chloride solution having a concentration such that the formulation is isotonic relative to normal body fluid. In addition to the carrier, the liquid formulations may contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitan monopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Non-aerosol formulations for inhalation may also comprise dry powder formulations, particularly insufflations in which the powder has an average particle size of from about 0.1 µm to about 50 µm, preferably from about 1 µm to about 25 µm.

Topical Formulations

Topical formulations may be in any form suitable for application to the body surface, and may comprise, for example, an ointment, cream, gel, lotion, solution, paste or the like, and/or may be prepared so as to contain liposomes, micelles, and/or microspheres. Preferred topical formulations herein are ointments, creams and gels.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, supra, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight (See, e.g., Remington: The Science and Practice of Pharmacy, supra).

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels-are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation; suitable enhancers are as described elsewhere herein.

Transdermal Administration

The compounds of the invention may also be administered through the skin or mucosal tissue using conventional transdermal drug delivery systems, wherein the agent is contained within a laminated structure (typically referred to as a transdermal "patch") that serves as a drug delivery device to be affixed to the skin. Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present, the backing is preferably made of a sheet or film of a flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, those enhancers listed above in transmucosal compositions.

Parenteral Administration

Parenteral administration, if used, is generally characterized by injection, including intramuscular, intraperitoneal, intravenous (IV) and subcutaneous injection. Injectable formulations can be prepared in conventional forms, either as liquid solutions or suspensions; solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. A more recently revised approach for parenteral administration involves use of a slow release or sustained release system (See, e.g., U.S. Pat. No. 3,710,795).

Intrathecal Administration

Intrathecal administration, if used, is generally characterized by administration directly into the intrathecal space (where fluid flows around the spinal cord).

One common system utilized for intrathecal administration is the APT Intrathecal treatment system available from Medtronic, Inc. APT Intrathecal uses a small pump that is surgically placed under the skin of the abdomen to deliver medication directly into the intrathecal space. The medication is delivered through a small tube called a catheter that is also surgically placed. The medication can then be administered directly to cells in the spinal cord involved in conveying sensory and motor signals associated with non-inflammatory GI tract disorders.

Another system available from Medtronic that is commonly utilized for intrathecal administration is the is the fully implantable, programmable SynchroMed® Infusion System. The SynchroMed® Infusion System has two parts that are both placed in the body during a surgical procedure: the catheter and the pump. The catheter is a small, soft tube. One end is connected to the catheter port of the pump, and the other end is placed in the intrathecal space. The pump is a round metal device about one inch (2.5 cm) thick, three inches (8.5 cm) in diameter, and weighs about six ounces (205 g) that stores and releases prescribed amounts of medication directly into the intrathecal space. It is made of titanium, a lightweight, medical-grade metal. The reservoir is the space inside the pump that holds the medication. The fill port is a raised center portion of the pump through which the pump is refilled. The doctor or a nurse inserts a needle through the patient's skin and through the fill port to fill the pump. Some pumps have a side catheter access port that allows the doctor to inject other medications or sterile solutions directly into the catheter, bypassing the pump.

The SynchroMed® pump automatically delivers a controlled amount of medication through the catheter to the intrathecal space around the spinal cord, where it is most effective. The exact dosage, rate and timing prescribed by the doctor are entered in the pump using a programmer, an external computer-like device that controls the pump's memory. Information about the patient's prescription is stored in the pump's memory. The doctor can easily review this information by using the programmer. The programmer communicates with the pump by radio signals that allow the doctor to tell how the pump is operating at any given time. The doctor also can use the programmer to change your medication dosage.

Methods of intrathecal administration may include those described above available from Medtronic, as well as other methods that are known to one of skill in the art.

Additional Dosage Formulations and Drug Delivery Systems

As compared with traditional drug delivery approaches, some controlled release technologies rely upon the modification of both macromolecules and synthetic small molecules to allow them to be actively instead of passively absorbed into the body. For example, XenoPort Inc. utilizes technology that takes existing molecules and re-engineers them to create new chemical entities (unique molecules) that have improved pharmacologic properties to either: 1) lengthen the short half-life of a drug; 2) overcome poor absorption; and/or 3) deal with poor drug distribution to target tissues. Techniques to lengthen the short half-life of a drug include the use of prodrugs with slow cleavage rates to release drugs over time or that engage transporters in small and large intestines to allow the use of oral sustained delivery systems, as well as drugs that engage active transport systems. Examples of such controlled release formulations, tablets, dosage forms, and drug delivery systems, and that are suitable for use with the present invention, are described in the following published US and PCT patent applications assigned to Xenoport Inc.: US20030158254; US20030158089; US20030017964; US2003130246; WO02100172; WO02100392; WO02100347; WO02100344; WO0242414; WO0228881; WO0228882; WO0244324; WO0232376; WO0228883; and WO0228411.

Some other controlled release technologies rely upon methods that promote or enhance gastric retention, such as those developed by Depomed Inc. Because many drugs are best absorbed in the stomach and upper portions of the small intestine, Depomed has developed tablets that swell in the stomach during the postprandial or fed mode so that they are treated like undigested food. These tablets therefore sit safely and neutrally in the stomach for 6, 8, or more hours and deliver drug at a desired rate and time to upper gastrointestinal sites. Specific technologies in this area include: 1) tablets that slowly erode in gastric fluids to deliver drugs at almost a constant rate (particularly useful for highly insoluble drugs); 2) bi-layer tablets that combine drugs with different characteristics into a single table (such as a highly insoluble drug in an erosion layer and a soluble drug in a diffusion layer for sustained release of both); and 3) combination tablets that can either deliver drugs simultaneously or in sequence over a desired period of time (including an initial burst of a fast acting drug followed by slow and sustained delivery of another drug). Examples of such controlled release formulations that are suitable for use with the present invention and that rely upon gastric retention during the postprandial or fed mode, include tablets, dosage forms, and drug delivery systems in the following US patents assigned to Depomed Inc.: U.S. Pat. No. 6,488,962; U.S. Pat. No. 6,451,808; U.S. Pat. No. 6,340,475; U.S. Pat. No. 5,972,389; U.S. Pat. No. 5,582,837; and U.S. Pat. No. 5,007,790. Examples of such controlled release formulations that are suitable for use with the present invention and that rely upon gastric retention during the postprandial or fed mode, include tablets, dosage forms, and drug delivery systems in the following published US and PCT patent applications assigned to Depomed Inc.: US20030147952; US20030104062; US20030104053; US20030104052; US20030091630; US20030044466; US20030039688; US20020051820; WO0335040; WO0335039; WO0156544; WO0132217; WO9855107; WO9747285; and WO9318755.

Other controlled release systems include those developed by ALZA Corporation based upon: 1) osmotic technology for oral delivery; 2) transdermal delivery via patches; 3) liposomal delivery via intravenous injection; 4) osmotic technology for long-term delivery via implants; and 5) depot technology designed to deliver agents for periods of days to a month. ALZA oral delivery systems include those that employ osmosis to provide precise, controlled drug delivery for up to 24 hours for both poorly soluble and highly soluble drugs, as well as those that deliver high drug doses meeting high drug loading requirements. ALZA controlled transdermal delivery systems provide drug delivery through intact skin for as long as one week with a single application to improve drug absorption and deliver constant amounts of drug into the bloodstream over time. ALZA liposomal delivery systems involve lipid nanoparticles that evade recognition by the immune system because of their unique polyethylene glycol (PEG) coating, allowing the precise delivery of drugs to disease-specific areas of the body. ALZA also has developed osmotically driven systems to enable the continuous delivery of small drugs, peptides, proteins, DNA and other bioactive macromolecules for up to one year for systemic or tissue-specific therapy. Finally, ALZA depot injection therapy is designed to deliver biopharmaceutical agents and small molecules for periods of days to a month using a nonaqueous polymer solution for the stabilization of macromolecules and a unique delivery profile.

Examples of controlled release formulations, tablets, dosage forms, and drug delivery systems that are suitable for use with the present invention are described in the following US patents assigned to ALZA Corporation: U.S. Pat. No. 4,367,741; U.S. Pat. No. 4,402,695; U.S. Pat. No. 4,418,038; U.S. Pat. No. 4,434,153; U.S. Pat. No. 4,439,199; U.S. Pat. No. 4,450,198; U.S. Pat. No. 4,455,142; U.S. Pat. No. 4,455,144; U.S. Pat. No. 4,484,923; U.S. Pat. No. 4,486,193; U.S. Pat. No. 4,489,197; U.S. Pat. No. 4,511,353; U.S. Pat. No. 4,519,801; U.S. Pat. No. 4,526,578; U.S. Pat. No. 4,526,933; U.S. Pat. No. 4,534,757; U.S. Pat. No. 4,553,973; U.S. Pat. No. 4,559,222; U.S. Pat. No. 4,564,364; U.S. Pat. No. 4,578,075; U.S. Pat. No. 4,588,580; U.S. Pat. No. 4,610,686; U.S. Pat. No. 4,612,008; U.S. Pat. No. 4,618,487; U.S. Pat. No. 4,627,851; U.S. Pat. No. 4,629,449; U.S. Pat. No. 4,642,233; U.S. Pat. No. 4,649,043; U.S. Pat. No. 4,650,484; U.S. Pat. No. 4,659,558; U.S. Pat. No. 4,661,105; U.S. Pat. No. 4,662,880; U.S. Pat. No. 4,675,174; U.S. Pat. No. 4,681,583; U.S. Pat. No. 4,684,524; U.S. Pat. No. 4,692,336; U.S. Pat. No. 4,693,895; U.S. Pat. No. 4,704,119; U.S. Pat. No. 4,705,515; U.S. Pat. No. 4,717,566; U.S. Pat. No. 4,721,613; U.S. Pat. No. 4,723,957; U.S. Pat. No. 4,725,272; U.S. Pat. No. 4,728,498; U.S. Pat. No. 4,743,248; U.S. Pat. No. 4,747,847; U.S. Pat. No. 4,751,071; U.S. Pat. No. 4,753,802; U.S. Pat. No. 4,755,180; U.S. Pat. No. 4,756,314; U.S. Pat. No. 4,764,380; U.S. Pat. No. 4,773,907; U.S. Pat. No. 4,777,049; U.S. Pat. No. 4,781,924; U.S. Pat. No. 4,783,337; U.S. Pat. No. 4,786,503; U.S. Pat. No. 4,788,062; U.S. Pat. No. 4,810,502; U.S. Pat. No. 4,812,313; U.S. Pat. No. 4,816,258; U.S. Pat. No. 4,824,675; U.S. Pat. No. 4,834,979; U.S. Pat. No. 4,837,027; U.S. Pat. No. 4,842,867; U.S. Pat. No. 4,846,826; U.S. Pat. No. 4,847,093; U.S. Pat. No. 4,849,226; U.S. Pat. No. 4,851,229; U.S. Pat. No. 4,851,231; U.S. Pat. No. 4,851,232; U.S. Pat. No. 4,853,229; U.S. Pat. No. 4,857,330; U.S. Pat. No. 4,859,470;

U.S. Pat. No. 4,863,456; U.S. Pat. No. 4,863,744; U.S. Pat. No. 4,865,598; U.S. Pat. No. 4,867,969; U.S. Pat. No. 4,871,548; U.S. Pat. No. 4,872,873; U.S. Pat. No. 4,874,388; U.S. Pat. No. 4,876,093; U.S. Pat. No. 4,892,778; U.S. Pat. No. 4,902,514; U.S. Pat. No. 4,904,474; U.S. Pat. No. 4,913,903; U.S. Pat. No. 4,915,949; U.S. Pat. No. 4,915,952; U.S. Pat. No. 4,917,895; U.S. Pat. No. 4,931,285; U.S. Pat. No. 4,946,685; U.S. Pat. No. 4,948,592; U.S. Pat. No. 4,954,344; U.S. Pat. No. 4,957,494; U.S. Pat. No. 4,960,416; U.S. Pat. No. 4,961,931; U.S. Pat. No. 4,961,932; U.S. Pat. No. 4,963,141; U.S. Pat. No. 4,966,769; U.S. Pat. No. 4,971,790; U.S. Pat. No. 4,976,966; U.S. Pat. No. 4,986,987; U.S. Pat. No. 5,006,346; U.S. Pat. No. 5,017,381; U.S. Pat. No. 5,019,397; U.S. Pat. No. 5,023,076; U.S. Pat. No. 5,023,088; U.S. Pat. No. 5,024,842; U.S. Pat. No. 5,028,434; U.S. Pat. No. 5,030,454; U.S. Pat. No. 5,071,656; U.S. Pat. No. 5,077,054; U.S. Pat. No. 5,082,668; U.S. Pat. No. 5,104,390; U.S. Pat. No. 5,110,597; U.S. Pat. No. 5,122,128; U.S. Pat. No. 5,125,894; U.S. Pat. No. 5,141,750; U.S. Pat. No. 5,141,752; U.S. Pat. No. 5,156,850; U.S. Pat. No. 5,160,743; U.S. Pat. No. 5,160,744; U.S. Pat. No. 5,169,382; U.S. Pat. No. 5,171,576; U.S. Pat. No. 5,176,665; U.S. Pat. No. 5,185,158; U.S. Pat. No. 5,190,765; U.S. Pat. No. 5,198,223; U.S. Pat. No. 5,198,229; U.S. Pat. No. 5,200,195; U.S. Pat. No. 5,200,196; U.S. Pat. No. 5,204,116; U.S. Pat. No. 5,208,037; U.S. Pat. No. 5,209,746; U.S. Pat. No. 5,221,254; U.S. Pat. No. 5,221,278; U.S. Pat. No. 5,229,133; U.S. Pat. No. 5,232,438; U.S. Pat. No. 5,232,705; U.S. Pat. No. 5,236,689; U.S. Pat. No. 5,236,714; U.S. Pat. No. 5,240,713; U.S. Pat. No. 5,246,710; U.S. Pat. No. 5,246,711; U.S. Pat. No. 5,252,338; U.S. Pat. No. 5,254,349; U.S. Pat. No. 5,266,332; U.S. Pat. No. 5,273,752; U.S. Pat. No. 5,284,660; U.S. Pat. No. 5,286,491; U.S. Pat. No. 5,308,348; U.S. Pat. No. 5,318,558; U.S. Pat. No. 5,320,850; U.S. Pat. No. 5,322,502; U.S. Pat. No. 5,326,571; U.S. Pat. No. 5,330,762; U.S. Pat. No. 5,338,550; U.S. Pat. No. 5,340,590; U.S. Pat. No. 5,342,623; U.S. Pat. No. 5,344,656; U.S. Pat. No. 5,348,746; U.S. Pat. No. 5,358,721; U.S. Pat. No. 5,364,630; U.S. Pat. No. 5,376,377; U.S. Pat. No. 5,391,381; U.S. Pat. No. 5,402,777; U.S. Pat. No. 5,403,275; U.S. Pat. No. 5,411,740; U.S. Pat. No. 5,417,675; U.S. Pat. No. 5,417,676; U.S. Pat. No. 5,417,682; U.S. Pat. No. 5,423,739; U.S. Pat. No. 5,424,289; U.S. Pat. No. 5,431,919; U.S. Pat. No. 5,443,442; U.S. Pat. No. 5,443,459; U.S. Pat. No. 5,443,461; U.S. Pat. No. 5,456,679; U.S. Pat. No. 5,460,826; U.S. Pat. No. 5,462,741; U.S. Pat. No. 5,462,745; U.S. Pat. No. 5,489,281; U.S. Pat. No. 5,499,979; U.S. Pat. No. 5,500,222; U.S. Pat. No. 5,512,293; U.S. Pat. No. 5,512,299; U.S. Pat. No. 5,529,787; U.S. Pat. No. 5,531,736; U.S. Pat. No. 5,532,003; U.S. Pat. No. 5,533,971; U.S. Pat. No. 5,534,263; U.S. Pat. No. 5,540,912; U.S. Pat. No. 5,543,156; U.S. Pat. No. 5,571,525; U.S. Pat. No. 5,573,503; U.S. Pat. No. 5,591,124; U.S. Pat. No. 5,593,695; U.S. Pat. No. 5,595,759; U.S. Pat. No. 5,603,954; U.S. Pat. No. 5,607,696; U.S. Pat. No. 5,609,885; U.S. Pat. No. 5,614,211; U.S. Pat. No. 5,614,578; U.S. Pat. No. 5,620,705; U.S. Pat. No. 5,620,708; U.S. Pat. No. 5,622,530; U.S. Pat. No. 5,622,944; U.S. Pat. No. 5,633,011; U.S. Pat. No. 5,639,477; U.S. Pat. No. 5,660,861; U.S. Pat. No. 5,667,804; U.S. Pat. No. 5,667,805; U.S. Pat. No. 5,674,895; U.S. Pat. No. 5,688,518; U.S. Pat. No. 5,698,224; U.S. Pat. No. 5,702,725; U.S. Pat. No. 5,702,727; U.S. Pat. No. 5,707,663; U.S. Pat. No. 5,713,852; U.S. Pat. No. 5,718,700; U.S. Pat. No. 5,736,580; U.S. Pat. No. 5,770,227; U.S. Pat. No. 5,780,058; U.S. Pat. No. 5,783,213; U.S. Pat. No. 5,785,994; U.S. Pat. No. 5,795,591; U.S. Pat. No. 5,811,465; U.S. Pat. No. 5,817,624; U.S. Pat. No. 5,824,340; U.S. Pat. No. 5,830,501; U.S. Pat. No. 5,830,502; U.S. Pat. No. 5,840,754; U.S. Pat. No. 5,858,407; U.S. Pat. No. 5,861,439; U.S. Pat. No. 5,863,558; U.S. Pat. No. 5,876,750; U.S. Pat. No. 5,883,135; U.S. Pat. No. 5,840,754; U.S. Pat. No. 5,897,878; U.S. Pat. No. 5,904,934; U.S. Pat. No. 5,904,935; U.S. Pat. No. 5,906,832; U.S. Pat. No. 5,912,268; U.S. Pat. No. 5,914,131; U.S. Pat. No. 5,916,582; U.S. Pat. No. 5,932,547; U.S. Pat. No. 5,938,654; U.S. Pat. No. 5,941,844; U.S. Pat. No. 5,955,103; U.S. Pat. No. 5,972,369; U.S. Pat. No. 5,972,370; U.S. Pat. No. 5,972,379; U.S. Pat. No. 5,980,943; U.S. Pat. No. 5,981,489; U.S. Pat. No. 5,983,130; U.S. Pat. No. 5,989,590; U.S. Pat. No. 5,995,869; U.S. Pat. No. 5,997,902; U.S. Pat. No. 6,001,390; U.S. Pat. No. 6,004,309; U.S. Pat. No. 6,004,578; U.S. Pat. No. 6,008,187; U.S. Pat. No. 6,020,000; U.S. Pat. No. 6,034,101; U.S. Pat. No. 6,036,973; U.S. Pat. No. 6,039,977; U.S. Pat. No. 6,057,374; U.S. Pat. No. 6,066,619; U.S. Pat. No. 6,068,850; U.S. Pat. No. 6,077,538; U.S. Pat. No. 6,083,190; U.S. Pat. No. 6,096,339; U.S. Pat. No. 6,106,845; U.S. Pat. No. 6,110,499; U.S. Pat. No. 6,120,798; U.S. Pat. No. 6,120,803; U.S. Pat. No. 6,124,261; U.S. Pat. No. 6,124,355; U.S. Pat. No. 6,130,200; U.S. Pat. No. 6,146,662; U.S. Pat. No. 6,153,678; U.S. Pat. No. 6,174,547; U.S. Pat. No. 6,183,466; U.S. Pat. No. 6,203,817; U.S. Pat. No. 6,210,712; U.S. Pat. No. 6,210,713; U.S. Pat. No. 6,224,907; U.S. Pat. No. 6,235,712; U.S. Pat. No. 6,245,357; U.S. Pat. No. 6,262,115; U.S. Pat. No. 6,264,990; U.S. Pat. No. 6,267,984; U.S. Pat. No. 6,287,598; U.S. Pat. No. 6,289,241; U.S. Pat. No. 6,331,311; U.S. Pat. No. 6,333,050; U.S. Pat. No. 6,342,249; U.S. Pat. No. 6,346,270; U.S. Pat. No. 6365183; U.S. Pat. No. 6,368,626; U.S. Pat. No. 6,387,403; U.S. Pat. No. 6,419,952; U.S. Pat. No. 6,440,457; U.S. Pat. No. 6,468,961; U.S. Pat. No. 6,491,683; U.S. Pat. No. 6,512,010; U.S. Pat. No. 6,514,530; U.S. Pat. No. 6534089; U.S. Pat. No. 6,544,252; U.S. Pat. No. 6,548,083; U.S. Pat. No. 6,551,613; U.S. Pat. No. 6,572,879; and U.S. Pat. No. 6,596,314.

Other examples of controlled release formulations, tablets, dosage forms, and drug delivery systems that are suitable for use with the present invention are described in the following published US patent application and PCT applications assigned to ALZA Corporation: US20010051183; WO0004886; WO0013663; WO0013674; WO0025753; WO0025790; WO0035419; WO0038650; WO0040218; WO0045790; WO0066126; WO0074650; WO0119337; WO0119352; WO0121211; WO0137815; WO0141742; WO0143721; WO0156543; WO3041684; WO03041685; WO03041757; WO03045352; WO03051341; WO03053400; WO03053401; WO9000416; WO9004965; WO9113613; WO9116884; WO9204011; WO9211843; WO9212692; WO9213521; WO9217239; WO9218102; WO9300071; WO9305843; WO9306819; WO9314813; WO9319739; WO9320127; WO9320134; WO9407562; WO9408572; WO9416699; WO9421262; WO9427587; WO9427589; WO9503823; WO9519174; WO9529665; WO9600065; WO9613248; WO9625922; WO9637202; WO9640049; WO9640050; WO9640139; WO9640364; WO9640365; WO9703634; WO9800158; WO9802169; WO9814168; WO9816250; WO9817315; WO9827962; WO9827963; WO9843611; WO9907342; WO9912526; WO9912527; WO9918159; WO9929297; WO9929348; WO9932096; WO9932153; WO9948494; WO9956730; WO9958115; and WO9962496.

Another drug delivery technology suitable for use in the present invention is that disclosed by DepoMed, Inc. in U.S. Pat. No.6,682,759, which discloses a method for manufacturing a pharmaceutical tablet for oral administration combining both immediate-release and prolonged-release modes of drug delivery. The tablet according to the method comprises a prolonged-release drug core and an immediate-release drug coating or layer, which can be insoluble or sparingly soluble in water. The method limits the drug particle diameter in the immediate-release coating or layer to 10 microns or less. The coating or layer is either the particles themselves, applied as an aqueous suspension, or a solid composition that contains the drug particles incorporated in a solid material that disintegrates rapidly in gastric fluid.

Andrx Corporation has also developed drug delivery technology suitable for use in the present invention that includes: 1) a pelletized pulsatile delivery system ("PPDS"); 2) a single composition osmotic tablet system ("SCOT"); 3) a solubility modulating hydrogel system ("SMHS"); 4) a delayed pulsatile hydrogel system ("DPHS"); 5) a stabilized pellet delivery system ("SPDS"); 6) a granulated modulating hydrogel system ("GMHS"); 7) a pelletized tablet system ("PELTAB"); 8) a porous tablet system ("PORTAB"); and 9) a stabilized tablet delivery system ("STDS"). PPDS uses pellets that are coated with specific polymers and agents to control the release rate of the microencapsulated drug and is designed for use with drugs that require a pulsed release. SCOT utilizes various osmotic modulating agents as well as polymer coatings to provide a zero-order drug release. SMHS utilizes a hydrogel-based dosage system that avoids the "initial burst effect" commonly observed with other sustained-release hydrogel formulations and that provides for sustained release without the need to use special coatings or structures that add to the cost of manufacturing. DPHS is designed for use with hydrogel matrix products characterized by an initial zero-order drug release followed by a rapid release that is achieved by the blending of selected hydrogel polymers to achieve a delayed pulse. SPDS incorporates a pellet core of drug and protective polymer outer layer, and is designed specifically for unstable drugs, while GMHS incorporates hydrogel and binding polymers with the drug and forms granules that are pressed into tablet form. PELTAB provides controlled release by using a water insoluble polymer to coat discrete drug crystals or pellets to enable them to resist the action of fluids in the gastrointestinal tract, and these coated pellets are then compressed into tablets. PORTAB provides controlled release by incorporating an osmotic core with a continuous polymer coating and a water soluble component that expands the core and creates microporous channels through which drug is released. Finally, STDS includes a dual layer coating technique that avoids the need to use a coating layer to separate the enteric coating layer from the omeprazole core.

Examples of controlled release formulations, tablets, dosage forms, and drug delivery systems that are suitable for use with the present invention are described in the following US patents assigned to Andrx Corporation: U.S. Pat. No. 5,397,574; U.S. Pat. No. 5,419,917; U.S. Pat. No. 5,458,887; U.S. Pat. No. 5,458,888; U.S. Pat. No. 5,472,708; U.S. Pat. No. 5,508,040; U.S. Pat. No. 5,558,879; U.S. Pat. No. 5,567,441; U.S. Pat. No. 5,654,005; U.S. Pat. No. 5,728,402; U.S. Pat. No. 5,736,159; U.S. Pat. No. 5,830,503; U.S. Pat. No. 5,834,023; U.S. Pat. No. 5,837,379; U.S. Pat. No. 5,916,595; U.S. Pat. No. 5,922,352; U.S. Pat. No. 6,099,859; U.S. Pat. No. 6,099,862; U.S. Pat. No. 6,103,263; U.S. Pat. No. 6,106,862; U.S. Pat. No. 6,156,342; U.S. Pat. No. 6,177,102; U.S. Pat. No. 6,197,347; U.S. Pat. No. 6,210,716; U.S. Pat. No. 6,238,703; U.S. Pat. No. 6,270,805; U.S. Pat. No. 6,284,275; U.S. Pat. No. 6,485,748; U.S. Pat. No. 6,495,162; U.S. Pat. No. 6,524,620; U.S. Pat. No. 6,544,556; U.S. Pat. No. 6,589,553; U.S. Pat. No. 6,602,522; and U.S. Pat. No. 6,610,326.

Examples of controlled release formulations, tablets, dosage forms, and drug delivery systems that are suitable for use with the present invention are described in the following published US and PCT patent applications assigned to Andrx Corporation: US20010024659; US20020115718; US20020156066; WO0004883; WO0009091; WO0012097; WO0027370; Wo0050010; WO0132161; WO0134123; WO0236077; WO0236100; WO02062299; WO02062824; WO02065991; WO02069888; WO02074285; WO03000177; WO9521607; WO9629992; WO9633700; WO9640080; WO9748386; WO9833488; WO9833489; WO9930692; WO9947125; and WO9961005.

Some other examples of drug delivery approaches focus on non-oral drug delivery, providing parenteral, transmucosal, and topical delivery of proteins, peptides, and small molecules. For example, the Atrigel® drug delivery system marketed by Atrix Laboratories Inc. comprises biodegradable polymers, similar to those used in biodegradable sutures, dissolved in biocompatible carriers. These pharmaceuticals may be blended into a liquid delivery system at the time of manufacturing or, depending upon the product, may be added later by a physician at the time of use. Injection of the liquid product subcutaneously or intramuscularly through a small gauge needle, or placement into accessible tissue sites through a cannula, causes displacement of the carrier with water in the tissue fluids, and a subsequent precipitate to form from the polymer into a solid film or implant. The drug encapsulated within the implant is then released in a controlled manner as the polymer matrix biodegrades over a period ranging from days to months. Examples of such drug delivery systems include Atrix's Eligard®, Atridox®/Doxirobe®, Atrisorb® FreeFlow™/Atrisorb®-D FreeFlow, bone growth products, and others as described in the following published US and PCT patent applications assigned to Atrix Laboratories Inc.: US RE37950; U.S. Pat. No. 6,630,155; U.S. Pat. No. 6,566,144; U.S. Pat. No. 6,610,252; U.S. Pat. No. 6,565,874; U.S. Pat. No. 6,528,080; U.S. Pat. No. 6,461,631; U.S. Pat. No. 6,395,293; U.S. Pat. No. 6,261,583; U.S. Pat. No. 6,143,314; U.S. Pat. No. 6,120,789; U.S. Pat. No. 6,071,530; U.S. Pat. No. 5,990,194; U.S. Pat. No. 5,945,115; U.S. Pat. No. 5,888,533; U.S. Pat. No. 5,792,469; U.S. Pat. No. 5,780,044; U.S. Pat. No. 5,759,563; U.S. Pat. No. 5,744,153; U.S. Pat. No. 5,739,176; U.S. Pat. No. 5,736,152; U.S. Pat. No. 5,733,950; U.S. Pat. No. 5,702,716; U.S. Pat. No. 5,681,873; U.S. Pat. No. 5,660,849; U.S. Pat. No. 5,599,552; U.S. Pat. No. 5,487,897; U.S. Pat. No. 5,368,859; U.S. Pat. No. 5,340,849; U.S. Pat. No. 5,324,519; U.S. Pat. No. 5,278,202; U.S. Pat. No. 5,278,201; US20020114737, US20030195489; US20030133964; US 20010042317; US20020090398; US20020001608; and US2001042317.

Atrix Laboratories Inc. also markets technology for the non-oral transmucosal delivery of drugs over a time period from minutes to hours. For example, Atrix's BEMA™ (Bioerodible Muco-Adhesive Disc) drug delivery system comprises pre-formed bioerodible discs for local or systemic delivery. Examples of such drug delivery systems include those as described in U.S. Pat. No. 6,245,345.

Other drug delivery systems marketed by Atrix Laboratories Inc. focus on topical drug delivery. For example, SMP™ (Solvent Particle System) allows the topical delivery of highly water-insoluble drugs. This product allows for a controlled amount of a dissolved drug to permeate the epidermal layer of the skin by combining the dissolved drug with a microparticle suspension of the drug. The SMP™ system works in stages whereby: 1) the product is applied to the skin surface; 2) the product near follicles concentrates at the skin pore; 3) the drug readily partitions into skin oils; and 4) the drug diffuses throughout the area. By contrast, MCA® (Mucocutaneous Absorption System) is a water-resistant topical gel providing sustained drug delivery. MCA® forms a tenacious film for either wet or dry surfaces where: 1) the product is applied to the skin or mucosal surface; 2) the product forms a tenacious moisture-resistant film; and 3) the adhered film provides sustained release of drug for a period from hours to days. Yet another product, BCP™ (Biocompatible Polymer System) provides a non-cytotoxic gel or liquid that is applied as a protective film for wound healing. Examples of these systems include Orajel™-Ultra Mouth Sore Medicine as well as those as described in the following published US patents and applications assigned to Atrix Laboratories Inc.: U.S. Pat. No. 6,537,565; U.S. Pat. No. 6,432,415; U.S. Pat. No. 6,355,657; U.S. Pat. No. 5,962,006; U.S. Pat. No. 5,725,491; U.S. Pat. No. 5,722,950; U.S. Pat. No. 5,717,030; U.S. Pat. No. 5,707,647; U.S. Pat. No. 5,632,727; and US20010033853.

Dosage and Administration

The concentration of the active agent in any of the aforementioned dosage forms and compositions can vary a great deal, and will depend on a variety of factors, including the type of composition or dosage form, the corresponding mode of administration, the nature and activity of the specific active agent, and the intended drug release profile. Preferred dosage forms contain a unit dose of active agent, i.e., a single therapeutically effective dose. For creams, ointments, etc., a "unit dose" requires an active agent concentration that provides a unit dose in a specified quantity of the formulation to be applied. The unit dose of any particular active agent will depend, of course, on the active agent and on the mode of administration.

For a Cav2.2 subunit calcium channel modulator, the unit dose for oral, transmucosal, topical, transdermal, and parenteral administration will be in the range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg.

Alternatively, for a Cav2.2 subunit calcium channel modulator, the unit dose for oral, transmucosal, topical, transdermal, and parenteral administration will be equal to or greater than about 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µg, about 100 µg, about 200 µg, about 300 µg, about 400 µg, about 500 µg, about 0.5 mg, about 1 mg, about 1.25 mg, about 1.5 mg, about 2.0 mg, about 2.5 mg, about 3.0 mg, about 3.5 mg, about 4.0 mg, about 4.5 mg, about 5 mg, about 10 mg, about 20 mg, about 30 mg, about 40 mg, about 50 mg, about 100 mg, about 200 mg, about 300 mg, about 400 mg, about 500 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg.

For a Cav2.2 subunit calcium channel modulator, the unit dose for intrathecal administration the unit dose for intrathecal administration will be in the range of from about 1 fg to about 1 mg, about 5 fg to about 500 µg, about 10 fg to about 400 µg, about 20 fg to about 300 µg, about 30 fg to about 200 µg, about 40 fg to about 100 µg, about 50 fg to about 50 µg, about 100 fg to about 40 µg, about 200 fg to about 30 µg, about 300 fg to about 20 µg, about 400 fg to about 10 µg, about 500 fg to about 5 µg, about 1 pg to about 1 µg, about 5 pg to about 500 ng, about 10 pg to about 400 ng, about 20 pg to about 300 ng, about 30 pg to about 200 ng, about 40 pg to about 100 ng, about 50 pg to about 50 ng, about 100 pg to about 40 ng, about 200 pg to about 30 ng, about 300 pg to about 20 ng, about 400 pg to about 10 ng, or about 500 pg to about 5 ng.

Alternatively, for a Cav2.2 subunit calcium channel modulator, the unit dose for intrathecal administration will be equal to or greater than about 1 fg, about 5 fg, about 10 fg, about 20 fg, about 30 fg, about 40 fg, about 50 fg, about 100 fg, about 200 fg, about 300 fg, about 400 fg, about 500 fg, about 1 pg, about 5 pg, about 10 pg, about 20 pg, about 30 pg, about 40 pg, about 50 pg, about 100 pg, about 200 pg, about 300 pg, about 400 pg, about 500 pg, about 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µg, about 100 µg, about 200 µg, about 300 µg, about 400 µg, or about 500 µ.

In a preferred embodiment, drug administration is on an as-needed basis, and does not involve chronic drug administration. With an immediate release dosage form, as-needed administration may involve drug administration immediately prior to commencement of an activity wherein suppression of the symptoms of a non-inflammatory GI tract disorder would be desirable, but will generally be in the range of from about 0 minutes to about 10 hours prior to such an activity, preferably in the range of from about 0 minutes to about 5 hours prior to such an activity, most preferably in the range of from about 0 minutes to about 3 hours prior to such an activity. With a sustained release dosage form, a single dose can provide therapeutic efficacy over an extended time period in the range of from about 1 hour to about 72 hours, typically in the range of from about 8 hours to about 48 hours, depending on the formulation. That is, the release period may be varied by the selection and relative quantity of particular sustained release polymers. If necessary, however, drug administration may be carried out within the context of an ongoing dosage regimen, i.e., on a weekly basis, twice weekly, daily, etc.

Packaged Kits

In another embodiment, a packaged kit is provided that contains the pharmaceutical formulation to be administered, i.e., a pharmaceutical formulation containing a therapeutically effective amount of a selected active agent for the treatment of non-inflammatory GI tract disorders, a container, preferably sealed, for housing the formulation during storage and prior to use, and instructions for carrying out drug administration in a manner effective to treat non-inflammatory GI tract disorders. The instructions will typically be written instructions on a package insert and/or on a label. Depending on the type of formulation and the intended mode of administration, the kit may also include a device for administering the formulation. The formulation may be any suitable formulation as described herein. For example, the formulation may be an oral dosage form containing a unit dosage of a selected active agent. The kit may contain multiple formulations of different dosages of the same agent. The kit may also contain multiple formulations of different active agents.

The kit may contain multiple formulations of different dosages of the same agent. The kit may also contain multiple formulations of different active agents. The kit may contain formulations suitable for sequential, separate and/or simultaneous use in the treatment of non-inflammatory GI tract disorders, and instructions for carrying out drug administration where the formulations are administered sequentially, separately and/or simultaneously in the treatment of non-inflammatory GI tract disorders.

The parts of the kit may be independently held in one or more containers—such as bottles, syringes, plates, wells, blister packs, or any other type of pharmaceutical packaging.

Insurance Claims

In general, the processing of an insurance claim for the coverage of a given medical treatment or drug therapy involves notification of the insurance company, or any other entity, that has issued the insurance policy against which the claim is being filed, that the medical treatment or drug therapy will be performed. A determination is then made as to whether the medical treatment or drug therapy that will be performed is covered under the terms of the policy. If covered, the claim is then processed, which can include payment, reimbursement, or application against a deductable.

The present invention encompasses a method for processing an insurance claim under an insurance policy for an active agent or pharmaceutically acceptable salts, esters, amides, prodrugs, or active metabolites thereof used in the treatment of non-inflammatory GI tract disorders, wherein said active agent or pharmaceutically acceptable salts, esters, amides, prodrugs, or active metabolites thereof are administered sequentially or concurrently in different compositions. This method comprises: 1) receiving notification that treatment using said active agent or pharmaceutically acceptable salts, esters, amides, prodrugs or active metabolites thereof will be performed or notification of a prescription; 2) determining whether said treatment using said active agent or pharmaceutically acceptable salts, esters, amides, prodrugs or active metabolites is covered under said insurance policy; and 3) processing said claim for treatment of said non-inflammatory GI tract disorders using said active agent or pharmaceutically acceptable salts, esters, amides, prodrugs, or active metabolites thereof, including payment, reimbursement, or application against a deductable. This method also encompasses the processing of claims for more than one active agent, whether they have been prescribed separately or concurrently for the treatment of non-inflammatory GI tract disorders.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

All patents, patent applications, and publications mentioned herein are hereby incorporated by reference in their entireties.

EXAMPLE

Methods for Treating Non-Inflammatory GI Tract Disorders Using Cav2.2 Subunit Calcium Channel Modulators The invention will be further described in the following examples, which do not limit the scope of the invention described in the claims. The following example illustrates the effects of administration of Cav2.2 subunit calcium channel modulators in a model for non-inflammatory GI tract disorders, and it is expected that these results will demonstrate the efficacy of Cav2.2 subunit calcium channel modulators for treatment of such disorders.

The experiments were designed to investigate the effect of a Cav2.2 subunit calcium channel modulator on voltage-activated calcium currents recorded from GI sensory neurons in vitro. The relationship between colon sensory neuron electrophysiology and GI function has been described by Su et al. (2000) *J Neurophysiol.* 84:836–843, and Su et al. (1998) *J Neurophysiol.* 80:3112–3119.

Example 1

Colonic Sensory Neuron Electrophysiology

Objective and Rationale

The objective of the current study was to determine the effect of Cav2.2 subunit calcium channel modulators on the ability to modulate calcium currents in GI tract primary afferent neurons, a commonly used model of GI tract disorders.

Methods

Labeling of GI tract afferent neurons: Adult female Sprague-Dawley rats (150–300 g) were deeply anesthetized with pentobarbital anesthesia and placed on isoflurane maintenance anesthesia. A ventral midline incision was made through the abdominal skin and musculature, exposing the GI tract. Five injections of the fluorescent dye Di-I (2 μl each of 25 mg/ml Di-I in DMSO) were made into the wall of the colon to label primary afferent fibers innervating the GI tract. The areas were rinsed with sterile saline to eliminate nonspecific spread of dye, and the incision was closed. Rats recovered for 5–12 days to allow for transport of fluorescent dye from distal terminals to the cell somata of dorsal root ganglion (DRG) neurons. Labeled neurons were identified in vitro using fluorescence optics Neuronal cultures: Fluorescent dye-injected rats were euthanized with pentobarbital anesthesia. For GI tract neurons, lumbosacral (L6, $S_1$) DRG were dissected from the vertebral column. Ganglia were placed separately in Dulbecco's modified Eagles medium (DMEM) containing 0.3% collagenase B for 40 min at 37° C. The cell solution was exchanged for a 0.25% trypsin in calcium/magnesium-free Dulbecco's phosphate-buffered saline solution, and further digested for 15 min at 37° C. Following a wash in fresh DMEM, ganglia were dissociated by a series of triturations using fire-polished Pasteur pipettes. DRG cells were plated on polylysine-treated glass coverslips. Cells were plated at a density of 0.5 ganglion per coverslip in 1 ml DMEM supplemented with 10% FBS, NGF, and 100 U/ml penicillin/streptomycin. All experimental procedures involving rats were conducted under a protocol approved by an Institutional Animal Care and Use Committee. Small variations in the concentrations of reagents, incubation times, etc. may occur and are expected to give similar results.

In most experiments, neurons were incubated in culture medium containing the FITC-labeled lectin BSI-B4 (IB4, 10 mg/ml) at 37° C. for 5 min before recording. The coverslip was washed with extracellular recording solution for 1 min before being placed in a recording chamber mounted on the stage of an inverted microscope equipped with fluorescence optics. Neuronal images were captured using a digital camera system.

Electrophysiology: All recordings were performed within 48 hours after dissociation. Dye-labeled primary afferent GI tract neurons were identified using an inverted phase contrast microscope with fluorescence optics. Neurons were selected for recording according to: 1) DiI-positive staining, indicating that they were GI tract afferent neurons; 2) IB4-negative staining, indicating that they are presumably peptidergic, TrKA-positive neurons; and 3) soma diameter <30 μm, indicating that they were presumably small diameter, C-fiber neurons. Whole-cell patch-clamp recordings were performed at room temperature. Fire polished patch electrodes had tip resistances of 1–4MΩ when filled with internal solution. Neurons were superfused at a flow rate of 1 ml/min with external solution.

Whole-cell patch-clamp experiments were performed using a MultiClamp 700A amplifier (Axon Instruments). Data were acquired, digitized at 5 kHz, and analyzed by pClamp software (Axon Instruments). Leak currents were subtracted by P/4 pulse protocol and series resistance was compensated by 50–70%.

Voltage clamp recordings used external and internal solutions that contained respectively (mM), 155 TEA-Cl, 5 $BaCl_2$, 10 glucose, 5 4-aminopyridine, 10 HEPES adjusted to pH 7.4 with TEA-OH (340 mOsm) and 140 KCl, 1 $CaCl_2$, 2 $MgCl_2$, 9 EGTA, 10 HEPES, 4 Mg ATP, 0.3 GTP (Tris Salt) adjusted to pH 7.4 with KOH (310 mOsm). All neurons were voltage-clamped at a holding potential of −80 mV. High voltage activated (HVA) calcium currents were elicited by depolarizing pulses to 0 mV at low frequency stimulation (10–15 s) and allowed to stabilize prior to compound application. In these experiments, barium was used as the charge carrier through calcium channels. Peak currents were measured for analysis of drug effects.

Omega-conotoxin GVIA was initially dissolved in $H_2O$ before final dilution in the external solution. It was then applied to neurons via bath perfusion.

All data are expressed as mean ±SEM.

Results and Conclusions

HVA calcium channel currents were evaluated in voltage clamp recordings using an external solution that suppressed sodium and potassium currents. Only GI tract afferent neurons were evaluated in this study. Omega-conotoxin GVIA (1 μM), a selective Cav2.2 calcium channel blocker, inhibited calcium current amplitudes evoked by depolarizing pulses (−80 to 0 mV) to 59±4% (n=3) of control amplitudes (FIGS. 1A, B). This represents the total Cav2.2 component contribution to HVA calcium channels recorded under the present conditions.

The ability of Cav2.2 subunit calcium channel modulators to modulate HVA calcium channel currents in GI tract afferent DRG neurons strongly indicates efficacy in mammalian forms of GI tract disorders.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. A method for treating a symptom of a non-inflammatory GI tract disorder, comprising administering a therapeutically effective amount of a Cav2.2 subunit calcium channel modulator selected from the group consisting of:
   a. ω-conotoxin GVIA; and
   b. ω-conotoxin MVIIA (Ziconotide).

2. The method of claim 1, wherein said Cav2.2 subunit calcium channel modulator is contained within a pharmaceutical formulation.

3. The method of claim 1, wherein said Cav2.2 subunit calcium channel modulator is administered on an as-needed basis.

4. The method of claim 3, wherein said Cav2.2 subunit calcium channel modulator is administered prior to commencement of an activity wherein suppression of the symptoms of a non-inflammatory GI tract disorder would be desirable.

5. The method of claim 4, wherein said Cav2.2 subunit calcium channel modulator is administered from about 0 to about 5 hours prior to commencement of an activity wherein suppression of said symptoms would be desirable.

6. The method of claim 4, wherein said Cav2.2 subunit calcium channel modulator is administered from about 0 to about 3 hours prior to commencement of an activity wherein suppression of said symptoms would be desirable.

7. The method of claim 1, wherein said Cav2.2 subunit calcium channel modulator is administered orally, transmucosally, sublingually, buccally, intranasally, transurethrally, rectally, by inhalation, topically, transdermally, parenterally, or intrathecally.

8. The method of claim 1, wherein the symptom of a non-inflammatory GI tract disorder is associated with a functional GI tract disorder selected from the group consisting of functional dysphagia, non-ulcer dyspepsia, irritable bowel syndrome, slow-transit constipation, and an evacuation disorder.

9. The method of claim 1, wherein the symptom of a non-inflammatory GI tract disorder is associated with a motor disorder of the esophagus selected from the group consisting of achalasia and diffuse esophageal spasm.

10. The method of claim 1, wherein the symptom of a non-inflammatory GI tract disorder is associated with a non-inflammatory structural GI disorder selected from the group consisting of hiatal hernia, stricture, esophageal web, Schatzki's ring, esophageal diverticulum, and esophageal scleroderma.

11. The method of claim 2, wherein the pharmaceutical formulation further comprises an additional active agent.

12. The method of claim 11, wherein the additional active agent is selected from the group consisting of: an antiulcerative, an antidiarrheal, a peristaltic colon stimulant, an antispasmodic, an antinauseant/prokinetic, an anti-inflammatory bowel drug, a tricyclic antidepressant, a ketolaric, duloxetine, venlafaxine, a selective serotonin reuptake inhibitor, a serotonin/norepinephrine reuptake inhibitor, a spasmolytic, an anticholinergic, gabapentin, pregabalin, a substituted aminomethyl-phenyl-cyclohexane derivative, a 5-HT$_3$ antagonist, a 5-HT$_4$ antagonist, a β3 adrenergic agonist, a neurokinin receptor antagonist, a bradykinin receptor antagonist, and a nitric oxide donor.

13. A pharmaceutical composition comprising a Cav2.2 subunit calcium channel modulator in a therapeutically effective amount sufficient to treat a symptom of a non-inflammatory GI tract disorder, wherein said Cav2.2 subunit calcium channel modulator is selected from the group consisting of:
   a. ω-conotoxin GVIA; and
   b. ω-conotoxin MVIIA (Ziconotide),
wherein the pharmaceutical formulation further comprises an additional active agent.

14. The pharmaceutical composition of claim 13, wherein the additional active agent is selected from the group consisting of: an antiulcerative, an antidiarrheal, a peristaltic colon stimulant, an antispasmodic, an antinauseant/prokinetic, an anti-inflammatory bowel drug, a tricyclic antidepressant, a ketolaric, duloxetine, venlafaxine, a selective serotonin reuptake inhibitor, a serotonin/norepinephrine reuptake inhibitor, a spasmolytic, an anticholinergic, gabapentin, pregabalin, a substituted aminomethyl-phenyl-cyclohexane derivative, a 5-$HT_3$ antagonist, a 5-$HT_4$ antagonist, a β3 adrenergic agonist, a neurokinin receptor antagonist, a bradykinin receptor antagonist, and a nitric oxide donor.

* * * * *

SEQUENCE LISTING

<160> NUMBER OF SEQ ID NOS: 2

<210> SEQ ID NO 1
<211> LENGTH: 33
<212> TYPE: PRT
<213> ORGANISM: Conus geographus
<220> FEATURE:
<221> NAME/KEY: VARIANT
<222> LOCATION: (0)...(0)
<223> OTHER INFORMATION: omega-conotoxin GVIA -continued

```
<400> SEQUENCE: 1

Cys Lys Ser His Tyr Pro Gly Ser Ser Cys Ser His Tyr Pro Thr Ser
1               5                   10                  15

Tyr Asn Cys Cys Arg Ser Cys Asn His Tyr Pro Tyr Thr Lys Arg Cys
            20                  25                  30

Tyr

<210> SEQ ID NO 2
<211> LENGTH: 25
<212> TYPE: PRT
<213> ORGANISM: Conus magus
<220> FEATURE:
<221> NAME/KEY: VARIANT
<222> LOCATION: (0)...(0)
<223> OTHER INFORMATION: omega-conotoxin MVIIA (Ziconotide)

<400> SEQUENCE: 2

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25
```